(12) United States Patent
Cuero Rengifo

(10) Patent No.: US 9,828,609 B2
(45) Date of Patent: Nov. 28, 2017

(54) BIOLOGICAL DEVICES AND METHODS FOR INCREASING THE PRODUCTION OF LYCOPENE FROM PLANTS

(71) Applicant: INTERNATIONAL PARK OF CREATIVITY, Bogota (CO)

(72) Inventor: Raul Cuero Rengifo, Cypress, TX (US)

(73) Assignee: International Park of Creativity, Bogota (CO)

( * ) Notice: Subject to any disclaimer, the term of this patent is extended or adjusted under 35 U.S.C. 154(b) by 8 days.

(21) Appl. No.: 14/774,769

(22) PCT Filed: Mar. 11, 2014

(86) PCT No.: PCT/IB2014/001232
§ 371 (c)(1),
(2) Date: Sep. 11, 2015

(87) PCT Pub. No.: WO2014/140924
PCT Pub. Date: Sep. 18, 2014

(65) Prior Publication Data
US 2016/0017362 A1    Jan. 21, 2016

Related U.S. Application Data

(60) Provisional application No. 61/776,903, filed on Mar. 12, 2013, provisional application No. 61/861,448, filed on Aug. 2, 2013.

(51) Int. Cl.
| | | |
|---|---|---|
| *C12N 15/82* | (2006.01) | |
| *C12N 9/02* | (2006.01) | |
| *C12N 9/90* | (2006.01) | |
| *C12P 5/00* | (2006.01) | |

(52) U.S. Cl.
CPC ....... *C12N 15/8279* (2013.01); *C12N 9/0073* (2013.01); *C12N 9/90* (2013.01); *C12P 5/007* (2013.01); *C12Y 114/13129* (2013.01); *C12Y 505/01018* (2013.01)

(58) Field of Classification Search
CPC ................................................. C12N 15/8279
See application file for complete search history.

(56) References Cited

U.S. PATENT DOCUMENTS

| | | |
|---|---|---|
| 2009/0220520 A1 | 9/2009 | Patell |
| 2011/0093965 A1 | 4/2011 | O'Donoghue et al. |
| 2012/0003630 A1 | 1/2012 | Collins et al. |
| 2012/0115208 A1 | 5/2012 | Ellison et al. |

FOREIGN PATENT DOCUMENTS

| | | |
|---|---|---|
| EP | 2371967 | 10/2011 |
| EP | 2434020 | 3/2012 |
| WO | 2007038276 | 4/2007 |

OTHER PUBLICATIONS

GenBank Accession U50739 May 1997.*
GenBank Accession AF408848 Oct. 2002.*
Tian, L. et al., The Plant Cell (Jun. 2003), vol. 15, pp. 1320-1332.*
Ruiz Sola, M.Aguila and Rodriguez-Concepcion, M. in the *Arabidopsis* Book; published Jan. 19, 2012; American Society of Plant Biologists, pp. 1-28.*
Kasuza Research Institute, Nature (Dec. 14, 2000), vol. 408 pp. 823-826.*
Nat. Center for Biotech. Info Protein Database, GenBank CAE06806.1, "beta-carotene hydroxylase," accessed Sep. 17, 2015.
International Search Report and Written Opinion for PCB/IB2014/001232 dated Nov. 6, 2014.
Nat. Center for Biotech. Info., Protein Databse, GenBank ABU93262.1, "lycopene epsilon-cyclase," accessed Sep. 17, 2014.
Hundle et al., "In vitro expression and activity of lycopene cyclase and beta-carotene hydroxylase from Erwinia herbicola," FEBS J. 1993, 315:329-334.

* cited by examiner

*Primary Examiner* — Russell Kallis
(74) *Attorney, Agent, or Firm* — Gardner Groff Greenwald & Villanueva, PC

(57) ABSTRACT

Described herein are devices and methods for enhancing the physiological properties of plants. For example, the devices and methods described herein increase the production of lycopene, which has industrial and economic value. The lycopene produced by the devices and methods does not require the ultra purification that is common in conventional or commercial methods. The devices and methods described herein also enhance the growth rate of plants.

21 Claims, 2 Drawing Sheets

BIOLOGICAL DEVICES AND METHODS FOR INCREASING THE PRODUCTION OF LYCOPENE FROM PLANTS

CROSS REFERENCE TO RELATED APPLICATIONS

This application claims priority upon U.S. provisional application Ser. No. 61/776,903, filed Mar. 12, 2013, and U.S. provisional application Ser. No. 61/861,448, filed Aug. 2, 2013. These applications are hereby incorporated by reference in their entireties for all of their teachings.

CROSS REFERENCE TO SEQUENCE LISTING

The genetic components described herein are referred to by a sequence identifier number (SEQ ID NO). The SEQ ID NO corresponds numerically to the sequence identifiers <400>1, <400>2, etc. The Sequence Listing, in written computer readable format (CFR), is incorporated by reference in its entirety.

BACKGROUND

Tissue culturing is used in the propagation of new plant varieties, the production of doubled haploids, cryopreservation, conservation of rare and endangered plants, cultivation of difficult-to-propagate plants, and the production of secondary metabolites and transgenic plants. Tissue culturing focuses on the production of high quality, disease-free plant materials for the growth of crop plants and fruit trees. However, major challenges are still associated with the production and distribution of high quality plant materials for plant breeding and the rapid production of improved plants. Currently, tissue culturing is used particularly for large-scale plant multiplication and micro-propagation, techniques which have many applications in forestry and agriculture. Hundreds of commercial micro-propagation laboratories worldwide are currently multiplying large numbers of clones of desired varieties and local flora.

Different opinions among members of the general public have been established regarding plant transformation, particularly by those highly concerned about environmental issues. By contrast, scientists recognize that the plant that results from a specific targeted genetic alteration is indistinguishable from the plant that has been developed by a process of breeding and selection. The only difference is that the process of altering a target plant can be greatly accelerated because the genetic modifications can be directed rather than random. Directed modification by homologous recombination has been tested with homologous-recombination dependent gene targeting (hrdGT). The problem with this approach is that the relative rate of homologous recombination compared to the rate of random insertion by illegitimate recombination is lower in plant cells than it is in animal cells. Efforts to address this limitation by the expression of foreign genes in plant cells have been made. These methods have had limited success in producing effective gene targeting. Moreover, even when these modified cells are used to effect homologous recombination, the resultant modified cell would still contain an exogenous gene used to select the homologous recombinants, and would thus still be considered a genetically modified plant by regulators and environmentally concerned entities.

Other methods in which homologous recombination is not involved, as well as the utilization of specific recombination sites and recombinases derived from transposons, have also been described in WO 01/85969 and WO 99/25821. The problem with this approach is the mixed structure of the oligonucleotide would likely prevent true recombination by genomic integration.

One of the most common techniques to genetically hybridize plants is the use of plasmid-carrying *Agrobacterium tumefaciens*. A part of the life cycle of the *A. tumefaciens* plasmid involves infection of plants. *A. tumefaciens* introduces the plasmid into the nuclei of plant cells in the form of single strands. A recombinant *A. tumefaciens* plasmid can be used to introduce exogenous DNA into a plant cell.

Different bacterial plasmid gene treatments have also been used. For example, a simple DNA recombinant plasmid or a plasmid holding specific gene cassettes to ensure homologous recombination has been used. However, plants hybridized by this method would be classified as genetically-modified organisms (GMOs) and would still pose problems for the food and pharmaceutical industries.

Methods for increasing size and yield of transgenic plants, as well as delaying flowering in the plants, using nucleic acids that encode plant transcription factors, have been established. (U.S. Pat. No. 7,858,848) However, these methods also involve genetically transforming the plants. Moreover, the extraction of secondary metabolites usually requires high initial amounts of plant biomass or material. In general, the extraction of plant metabolites is carried out from large amounts of fresh biomass material, which requires agronomic practices, the use of chemicals, and time consuming and expensive extraction methods.

SUMMARY

Described herein are devices and methods for enhancing the physiological properties of plants. For example, the biological devices and methods described herein increase the production of lycopene, which has industrial and economic value. The lycopene produced by the devices and methods does not require the ultra purification that is common in conventional or commercial methods. The devices and methods described herein also enhance the growth rate of plants.

The advantages of the invention will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
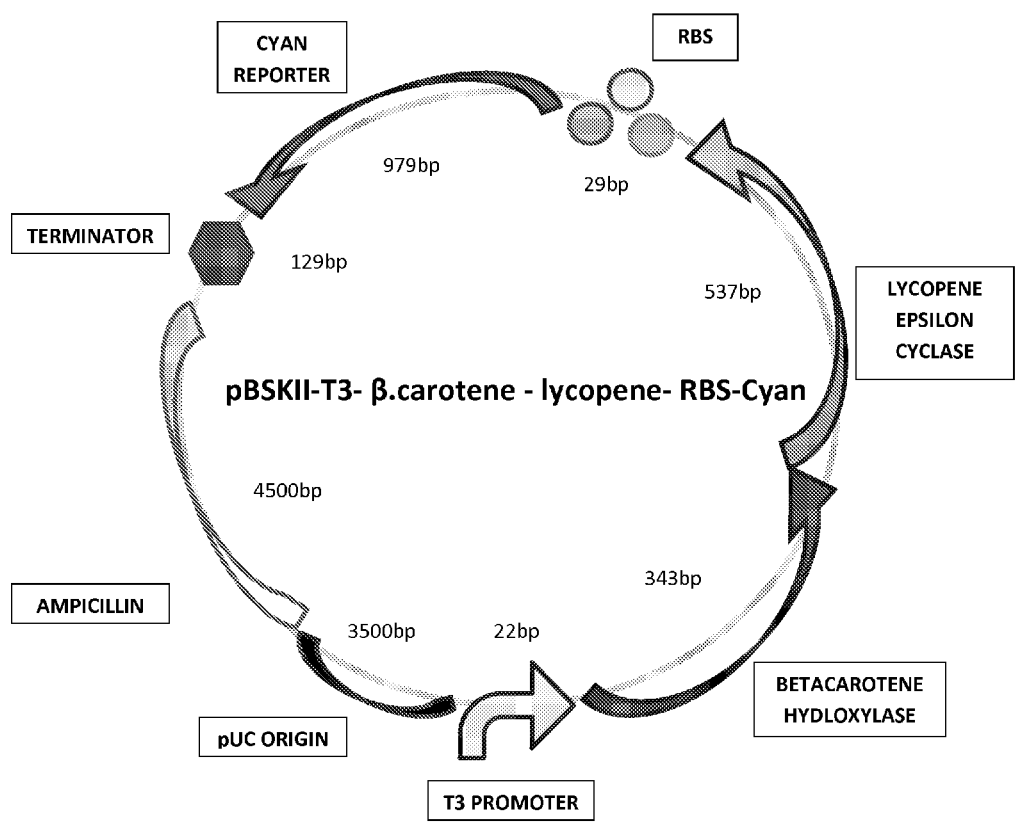
FIG. 1 shows a DNA construct, described herein, incorporated in a plasmid.

Before the present compounds, compositions, articles, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "an isolated nucleic acid" includes mixtures of two or more such nucleic acids, and the like.

"Optional" or "optionally" means that the subsequently described event or circumstance can or cannot occur, and that the description includes instances where the event or circumstance occurs and instances where it does not. For example, the phrase "optionally includes a gene for a selective marker" means that the gene may or may not be present.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combination and permutation of these compounds may not be explicitly disclosed, each is specifically contemplated and described herein. For example, if a bacterium is disclosed and discussed and a number of different compatible bacterial plasmids are discussed, each and every combination and permutation of bacterium and bacterial plasmid that is possible is specifically contemplated unless specifically indicated to the contrary. For example, if a class of molecules A, B, and C are disclosed as well as a class of molecules D, E, and F, and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E is specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, If a variety of additional steps can be performed, it is understood that each of these additional steps can be performed with any specific embodiment or combination of embodiments of the disclosed methods, and that each such combination is specifically contemplated and should be considered disclosed.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Described herein are devices and methods for enhancing the physiological properties of a plant. The term "physiological property" as defined herein includes any physical, chemical, or biological feature that is improved using the devices and methods described herein. In one aspect, the devices and methods can enhance the production of metabolites (e.g., lycopene) produced by the plant. In other aspects, the devices and methods can enhance the growth rate of the plant. These are just some of the physiological properties that are enhanced using the devices and methods described herein.

As used herein, "plant" is used in a broad sense to include, for example, any species of woody, ornamental, crop, cereal, fruit, or vegetable plant, as well as photosynthetic green algae. "Plant" also refers to a plurality of plant cells that are differentiated into a structure that is present at any stage of a plant's development. Such structures include, but are not limited to, fruits, shoots, stems, leaves, flower petals, roots, tubers, corms, bulbs, seeds, gametes, cotyledons, hypocotyls, radicles, embryos, gametophytes, tumors, and the like. "Plant cell," "plant cells," or "plant tissue" as used herein refers to differentiated and undifferentiated tissues of plants including those present in any of the tissues described above, as well as to cells in culture such as, for example, single cells, protoplasts, embryos, calluses, etc.

"Heterologous" genes and proteins are genes and proteins that have been experimentally put into a cell that are not normally expressed by that cell. A heterologous gene may be cloned or derived from a different cell type or species than the recipient cell or organism. Heterologous genes may be introduced into cells by transduction or transformation.

An "isolated" nucleic acid is one that has been separated from other nucleic acid molecules and/or cellular material (peptides, proteins, lipids, saccharides, and the like) normally present in the natural source of the nucleic acid. An "isolated" nucleic acid may optionally be free of the flanking sequences found on either side of the nucleic acid as it naturally occurs. An isolated nucleic acid can be naturally occurring, can be chemically synthesized, or can be a cDNA molecule (i.e., is synthesized from an mRNA template using reverse transcriptase and DNA polymerase enzymes).

"Transformation" or "transfection" as used herein refers to a process for introducing heterologous DNA into a host cell. Transformation can occur under natural conditions or may be induced using various methods known in the art.

Many methods for transformation are known in the art and the skilled practitioner will know how to choose the best transformation method based on the type of cells being transformed. Methods for transformation include, for example, viral infection, electroporation, lipofection, chemical transformation, and particle bombardment. Cells may be stably transformed (i.e., the heterologous DNA is capable of replicating as an autonomous plasmid or as part of the host chromosome) or may be transiently transformed (i.e., the heterologous DNA is expressed only for a limited period of time).

"Competent cells" refers to microbial cells capable of taking up heterologous DNA. Competent cells can be purchased from a commercial source, or cells may be made competent using procedures known in the art. Exemplary procedures for producing competent cells are provided in the Examples.

I. DNA Constructs and Biological Devices

The biological devices described herein can be used to enhance the physiological properties of a plant. In one aspect, the biological device can increase the production of a desired metabolite produced by the plant. The term "metabolite" as defined herein is any chemical compound produced by the plant, where it is desirable to produce increased quantities of the compound. Examples of metabolites include compounds having nutritional or medicinal value as well as any other commercial value. The device is generally composed of host cells, where the host cells are transformed with a DNA construct described herein that promotes the expression of the metabolite of interest in the plant cells.

It is understood that one way to define the variants and derivatives of the genetic components and DNA constructs described herein is through defining the variants and derivatives in terms of homology/identity to specific known sequences. Those of skill in the art readily understand how to determine the homology of two nucleic acids. For example, the homology can be calculated after aligning the two sequences so that the homology is at its highest level. Another way of calculating homology can be performed by published algorithms (see Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989, which are herein incorporated by reference for at least material related to nucleic acid alignment).

As used herein, "conservative" mutations are mutations that result in an amino acid change in the protein produced from a sequence of DNA. When a conservative mutation occurs, the new amino acid has similar properties as the wild type amino acid and generally does not drastically change the function or folding of the protein (e.g., switching isoleucine for valine is a conservative mutation since both are small, branched, hydrophobic amino acids). "Silent mutations," meanwhile, change the nucleic acid sequence of a gene encoding a protein but do not change the amino acid sequence of the protein.

It is understood that the description of conservative mutations and homology can be combined together in any combination, such as embodiments that have at least 70%, 75%, 80%, 85%, 90%, 95%, or 99% homology to a particular sequence wherein the variants are conservative mutations. It is understood that any of the sequences described herein can be a variant or derivative having the homology values listed above.

In one aspect, a database such as, for example, GenBank, can be used to determine the sequences of genes and/or regulatory regions of interest, the species from which these elements originate, and related homologous sequences.

In one aspect, the DNA construct described herein can promote the expression of metabolites such as, for example, lycopene, from plants. In one aspect, the DNA construct is from 5' to 3' the following genetic components in the following order: (a) a gene that expresses beta-carotene hydroxylase and (b) a gene that expresses lycopene epsilon-cyclase.

In one aspect, the gene that expresses beta-carotene hydroxylase is isolated from plants. In another aspect, the gene that expresses beta-carotene hydroxylase is isolated from bacteria. In one aspect, the bacteria are cyanobacteria. In a further aspect, the cyanobacteria are *Synechococcus* sp. WH8102, *Synechococcus elongatus* PCC6301 or PCC7942, or *Prochlorus marinus*. In a still further aspect, the *P. marinus* is subspecies *marinus*, strain CCMP1375. In a further aspect, the gene that expresses beta-carotene hydroxylase in the DNA construct has SEQ ID NO. 5 or a derivative or variant thereof. In another aspect, the gene that expresses beta-carotene hydroxylase in the DNA construct has SEQ ID NOS. 6 or 7 or a derivative or variant thereof.

In another aspect, the gene that expresses lycopene epsilon-cyclase is isolated from plants. In a further aspect, the plant is corn (*Zea mays*), sorghum or milo (*Sorghum bicolor*), or *Arabidopsis thaliana*. In another aspect, the gene that expresses lycopene epsilon-cyclase is isolated from bacteria. In a further aspect, the bacteria are *Xanthobacter autotrophicus* PY2. In a further aspect, the gene that expresses lycopene epsilon-cyclase in the DNA construct has SEQ ID NO. 8 or a derivative or variant thereof. In another aspect, the gene that expresses lycopene epsilon-cyclase in the DNA construct has SEQ ID NOS. 9 or 10 or a derivative or variant thereof.

In another aspect, the DNA construct further includes (c) a promoter, (d) a terminator or stop sequence, (e) a gene that confers resistance to an antibiotic (a "selective marker"), (f) a reporter protein, or a combination thereof.

In a further aspect, the DNA construct is from 5' to 3' the following genetic components in the following order: (1) a promoter, (2) a gene that expresses beta-carotene hydroxylase, (3) a gene that expresses lycopene epsilon-cyclase, and (4) a terminator or stop sequence.

In one aspect, a regulatory sequence is already incorporated into a vector such as, for example, a plasmid, prior to genetic manipulation of the vector. In another aspect, the regulatory sequence can be incorporated into the vector through the use of restriction enzymes or any other technique known in the art.

In one aspect, the regulatory sequence is a promoter. The term "promoter" refers to a DNA sequence capable of controlling the expression of a coding sequence. In one aspect, the coding sequence to be controlled is located 3' to the promoter. In another aspect, the promoter is derived from a native gene. In an alternative aspect, the promoter is composed of multiple elements derived from different genes and/or promoters. A promoter can be assembled from elements found in nature, from artificial and/or synthetic elements, or from a combination thereof. It is understood by those skilled in the art that different promoters can direct the expression of a gene in different tissues or cell types, at different stages of development, in response to different environmental or physiological conditions, and/or in different species. In one aspect, the promoter functions as a switch to activate the expression of a gene.

In one aspect, the promoter is "constitutive." A constitutive promoter is a promoter that causes a gene to be expressed in most cell types at most times. In another aspect, the promoter is "regulated." A regulated promoter is a promoter that becomes active in response to a specific stimulus. A promoter may be regulated chemically, such as, for example, in response to the presence or absence of a particular metabolite (e.g., lactose or tryptophan), a metal ion, a molecule secreted by a pathogen, or the like. A promoter may also be regulated physically, such as, for example, in response to heat, cold, water stress, salt stress, oxygen concentration, illumination, wounding, or the like.

Promoters that are useful to drive expression of the nucleotide sequences described herein are numerous and familiar to those skilled in the art. Suitable promoters include, but are not limited to, the following: T3 promoter, T7 promoter, Fe promoter, and GAL1 promoter. Variants of these promoters are also contemplated. The skilled artisan will be able to use site-directed mutagenesis and/or other mutagenesis techniques to modify the promoters to promote more efficient function. The promoter may be positioned, for example, from 10-100 nucleotides away from a ribosomal binding site.

In one aspect, the promoter is a T3 promoter. In another aspect, the T3 promoter in the DNA construct has SEQ ID NO. 1, 2, or a derivative or variant thereof. In another aspect, the promoter in the DNA construct has SEQ ID NO. 3, 4, or a derivative or variant thereof.

In a further aspect, the ribosomal binding site in the DNA construct comprises SEQ ID NOS. 11 or 12, or a derivative or variant thereof.

In another aspect, the regulatory sequence is a terminator or stop sequence. As used herein, a terminator is a sequence of DNA that marks the end of a gene or operon to be transcribed. In a further aspect, the terminator is an intrinsic terminator or a Rho-dependent transcription terminator. As used herein, an "intrinsic terminator" is a sequence wherein a hairpin structure can form in the nascent transcript and wherein the hairpin disrupts the mRNA/DNA/RNA polymerase complex. As used herein, a "Rho-dependent" transcription terminator requires a Rho factor protein complex to disrupt the mRNA/DNA/RNA polymerase complex.

In another aspect, the terminator in the DNA construct is SEQ ID NO. 13 or a derivative or variant thereof.

In a further aspect, the regulatory sequence includes both a promoter and a terminator or stop sequence. In a still further aspect, the regulatory sequence can include multiple promoters or terminators. Other regulatory elements, such as enhancers, are also contemplated. Enhancers may be located from about 1 to about 2000 nucleotides in the 5' direction from the start codon of the DNA to be transcribed, or may be located 3' to the DNA to be transcribed. Enhancers may be "cis-acting," that is, located on the same molecule of DNA as the gene whose expression they affect.

In another aspect, the DNA construct comprises the following components in the following sequence: a T3 promoter having SEQ ID NO. 1, a gene that expresses beta-carotene hydroxylase having SEQ ID NO. 4, a gene that expresses lycopene epsilon-cyclase having SEQ ID NO. 8, a ribosomal binding site having SEQ ID NO. 11, and a terminator having SEQ ID NO. 13.

In certain aspects, the DNA construct can include a gene that expresses a reporter protein. The selection of the reporter protein can vary. For example, the reporter protein can be a yellow fluorescent protein, red fluorescent protein, a green fluorescent protein, or a cyan fluorescent protein. In one aspect, the gene that expresses the reporter protein has SEQ ID NO. 14. The amount of fluorescence that is produced by the biological device can be correlated to the amount of DNA incorporated into the plant cells. The fluorescence produced by the device can be detected and quantified using techniques known in the art. For example, spectrofluorometers are typically used to measure fluorescence. The Examples provide exemplary procedures for measuring the amount of fluorescence as a result of the expression of DNA.

The DNA construct described herein can be part of a vector. In one aspect, the vector is a plasmid, a phagemid, a cosmid, a yeast artificial chromosome, a bacterial artificial chromosome, a virus, a phage, or a transposon.

In general, plasmid vectors containing replicon and control sequences that are derived from species compatible with the host cell are used in connection with these hosts. Vectors capable of high levels of expression of recombinant genes and proteins are well known in the art. The vector ordinarily carries a replication origin as well as marking sequences that are capable of providing phenotypic selection in transformed cells. Plasmid vectors useful for the transformation of a variety of host cells are well known and are commercially available. Such vectors include, but are not limited to, pWLNEO, pSV2CAT, pOG44, PXT1, pSG (Stratagene), pSVK3, pBSK, pBR322, pYES, pYES2, pBSKII, and pUC vectors.

Plasmids are double-stranded, autonomously-replicating, genetic elements that are not integrated into host cell chromosomes. Further, these genetic elements are usually not part of the host cell's central metabolism. In bacteria, plasmids may range from 1 kilobase (kb) to over 200 kb. Plasmids can be engineered to encode a number of useful traits including the production of secondary metabolites, antibiotic resistance, the production of useful proteins, degradation of complex molecules and/or environmental toxins, and others. Plasmids have been the subject of much research in the field of genetic engineering, as plasmids are convenient expression vectors for foreign DNA in, for example, microorganisms. Plasmids generally contain regulatory elements such as promoters and terminators and also usually have independent replication origins. Ideally, plasmids will be present in multiple copies per host cell and will contain selectable markers (such as genes for antibiotic resistance) to allow the ordinarily skilled artisan to select host cells that have been successfully transfected with the plasmids (for example, by culturing the host cells in a medium containing the antibiotic).

In one aspect, the vector encodes a selection marker. In a further aspect, the selection marker is a gene that confers resistance to an antibiotic. In certain aspects, during fermentation of host cells transformed with the vector, the cells are contacted with the antibiotic. For example, the antibiotic may be included in the culture medium. Cells that have not been successfully transformed cannot survive in the presence of the antibiotic; only cells containing the vector that confers antibiotic resistance can survive. Optionally, only cells containing the vector to be expressed will be cultured, as this will result in the highest production efficiency of the desired gene products (e.g., peptides involved in the synthesis of lycopene). Cells that do not contain the vector would otherwise compete with transformed cells for resources. In one aspect, the antibiotic is tetracycline, neomycin, kanamycin, ampicillin, hygromycin, chloramphenicol, amphotericin B, bacitracin, carbapenam, cephalosporin, ethambutol, fluoroquinolones, isonizid, methicillin, oxacillin, vancomycin, streptomycin, quinolines, rifampin, rifampicin, sulfonamides, cephalothin, erythromycin, streptomycin, gentamycin, penicillin, other commonly-used antibiotics, or a combination thereof.

In one aspect, when the vector is a plasmid, the plasmid can also contain a multiple cloning site or polylinker. In a further aspect, the polylinker contains recognition sites for multiple restriction enzymes. The polylinker can contain up to 2, 3, 4, 5, 6, 7, 8, 9, 10, 11, 12, 13, 14, 15, 16, 17, 18, 19, 20, or more than 20 recognition sites for restriction enzymes. Further, restriction sites may be added, disabled, or removed as required, using techniques known in the art. In one aspect, the plasmid contains restriction sites for any known restriction enzyme such as, for example, HindIII, KpnI, SacI, BamHI, BstXI, EcoRI, BsaBI, NotI, XhoI, SphI, SbaI, ApaI, SalI, ClaI, EcoRV, PstI, SmaI, XmaI, SpeI, EagI, SacII, or any combination thereof. In a further aspect, the plasmid contains more than one recognition site for the same restriction enzyme.

In one aspect, the restriction enzyme can cleave DNA at a palindromic or an asymmetrical restriction site. In a further aspect, the restriction enzyme cleaves DNA to leave blunt ends; in an alternative aspect, the restriction enzyme cleaves DNA to leave "sticky" or overhanging ends. In another aspect, the enzyme can cleave DNA a distance of from 20 bases to over 1000 bases away from the restriction site. A variety of restriction enzymes are commercially available and their recognition sequences, as well as instructions for use (e.g. amount of DNA needed, precise volumes of reagents, purification techniques, as well as information about salt concentration, pH, optimum temperature, incubation time, and the like) are made available by commercial enzyme suppliers.

In one aspect, a plasmid with a polylinker containing one or more restriction sites can be digested with one restriction enzyme and a nucleotide sequence of interest can be ligated into the plasmid using a commercially-available DNA ligase enzyme. Several such enzymes are available, often as kits containing all reagents and instructions required for use. In another aspect, a plasmid with a polylinker containing two or more restriction sites can be simultaneously digested with two restriction enzymes and a nucleotide sequence of interest can be ligated into the plasmid using a DNA ligase enzyme. Using two restriction enzymes provides an asymmetric cut in the DNA, allowing for insertion of a nucleotide sequence of interest in a particular direction and/or on a particular strand of the double-stranded plasmid. Since RNA synthesis from a DNA template proceeds from 5' to 3', often starting just after a promoter, the order and direction of elements inserted into a plasmid is especially important. If a plasmid is to be simultaneously digested with multiple restriction enzymes, these enzymes must be compatible in terms of buffer, salt concentration, and other incubation parameters.

In some aspects, prior to ligation using a ligase enzyme, a plasmid that has been digested with a restriction enzyme is treated with an alkaline phosphatase enzyme to remove 5' terminal phosphate groups. This prevents self-ligation of the plasmid and thus facilitates ligation of heterologous nucleic acid fragments into the plasmid.

In one aspect, the nucleic acids (e.g., genes that express beta-carotene hydroxylase and lycopene epsilon-cyclase) used in the DNA constructs described herein can be amplified using the polymerase chain reaction (PCR) prior to being ligated into a plasmid or other vector. Typically, PCR-amplification techniques make use of primers or short, chemically-synthesized oligonucleotides that are complementary to regions on each respective strand flanking the DNA or nucleotide sequence to be amplified. A person having ordinary skill in the art will be able to design or choose primers based on the desired experimental conditions. In general, primers should be designed to provide for efficient and faithful replication of the target nucleic acids. Two primers are required for the amplification of each gene, one for the sense strand (that is, the strand containing the gene of interest) and one for the antisense strand (that is, the strand complementary to the gene of interest). Pairs of primers should have similar melting temperatures that are close to the PCR reaction's annealing temperature. In order to facilitate the PCR reaction, the following features should be avoided in primers: mononucleotide repeats, complementarity with other primers in the mixture, self-complementarity, and internal hairpins and/or loops. Methods of primer design are known in the art; additionally, computer programs exist that can assist the ordinarily skilled practitioner with primer design. Primers can optionally incorporate restriction enzyme recognition sites at their 5' ends to assist in later ligation into plasmids or other vectors.

PCR can be carried out using purified DNA, unpurified DNA that has been integrated into a vector, or unpurified genomic DNA. The process for amplifying target DNA using PCR consists of introducing an excess of two primers having the characteristics described above to a mixture containing the sequence to be amplified, followed by a series of thermal cycles in the presence of a heat-tolerant or thermophilic DNA polymerase, such as, for example, any of Taq, Pfu, Pwo, Tfl, rTth, Tli, or Tma polymerases. A PCR "cycle" involves denaturation of the DNA through heating, followed by annealing of the primers to the target DNA, followed by extension of the primers using the thermophilic DNA polymerase and a supply of deoxynucleotide triphosphates (i.e., dCTP, dATP, dGTP, and TTP), along with buffers, salts, and other reagents as needed. In one aspect, the DNA segments created by primer extension during the PCR process can serve as templates for additional PCR cycles. Many PCR cycles can be performed to generate a large concentration of target DNA or gene. PCR can optionally be performed in a device or machine with programmable temperature cycles for denaturation, annealing, and extension steps. Further, PCR can be performed on multiple genes simultaneously in the same reaction vessel or microcentrifuge tube since the primers chosen will be specific to selected genes. PCR products can be purified by techniques known in the art such as, for example, gel electrophoresis followed by extraction from the gel using commercial kits and reagents.

In a further aspect, the vector can include an origin of replication, allowing it to use the host cell's replication machinery to create copies of itself.

As used herein, "operably linked" refers to the association of nucleic acid sequences on a single nucleic acid fragment so that the function of one affects the function of another. For example, if sequences for multiple genes are inserted into a single plasmid, their expression may be operably linked. Alternatively, a promoter is said to be operably linked with a coding sequence when it is capable of affecting the expression of the coding sequence.

As used herein, "expression" refers to transcription and/or accumulation of an mRNA derived from a gene or DNA fragment. Expression may also be used to refer to translation of mRNA into a peptide, polypeptide, or protein.

Exemplary methods for producing the DNA constructs described herein are provided in the Examples. Restriction enzymes and purification techniques known in the art can be used to prepare the DNA constructs. After the vector incorporating the DNA construct has been produced, it can be incorporated into host cells using the methods described below.

II. Biological Devices

In one aspect, a "biological device" is formed when a microbial cell is transfected with the DNA construct described herein. The biological devices are generally composed of microbial host cells, where the host cells are transformed with a DNA construct described herein.

In one aspect, the DNA construct is carried by the expression vector into the cell and is separate from the host cell's genome. In another aspect, the DNA construct is incorporated into the host cell's genome. In still another aspect, incorporation of the DNA construct into the host cell enables the host cell to produce lycopene.

The host cells as referred to herein include their progeny, which are any and all subsequent generations formed by cell division. It is understood that not all progeny may be identical due to deliberate or inadvertent mutations. A host cell may be "transfected" or "transformed," which refers to a process by which exogenous nucleic acid is transferred or introduced into the host cell. A transformed cell includes the primary subject cell and its progeny. The host cells can be naturally-occurring cells or "recombinant" cells. Recombinant cells are distinguishable from naturally-occurring cells in that naturally-occurring cells do not contain heterologous nucleic acid sequences introduced using molecular biology techniques. In one aspect, the host cell is a prokaryotic cell, such as, for example, *Bacillus pumilus* or *E. coli*. In other aspects, the host cell is yeast such as, for example, *Saccharomyces cerevisiae*. Host cells transformed with the DNA construct described herein are referred to as biological devices.

The DNA construct is first delivered into the host cell. This delivery may be accomplished in vitro, using well-developed laboratory procedures for transforming cell lines. Transformation of bacterial cell lines can be achieved using a variety of techniques. One method involves calcium chloride. The exposure to the calcium ions renders the cells able to take up the DNA construct. Another method is electroporation. In this technique, a high-voltage electric field is applied briefly to cells, producing transient holes in the cell membrane through which the vector containing the DNA construct enters. Exemplary procedures for transforming yeast and bacteria with specific DNA are provided in the Examples. In certain aspects, two or more types of DNA can be incorporated into the host cells. Thus, different metabolites can be produced from the same plant at enhanced rates.

Once the DNA construct has been incorporated into the host cell, the cells are cultured such that the cells multiply. A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. A variety of other carbon sources are contemplated, including, but not limited to: monosaccharides such as glucose and fructose, disaccharides such as lactose and sucrose, oligosaccharides, polysaccharides such as starch, and mixtures thereof. Unpurified mixtures extracted from feedstocks are also contemplated and can include molasses, barley malt, and related compounds and compositions. Other glycolytic and tricarboxylic acid cycle intermediates are also contemplated as carbon sources, as are one-carbon substrates such as carbon dioxide and/or methanol in the cases of compatible organisms. The carbon source utilized is limited only by the particular organism being cultured.

Furthermore, the use of different media results in different growth rates and different stationary phase densities. Secondary metabolite production is highest when cells are in stationary phase. A rich media results in a short doubling time and higher cell density at stationary phase. Minimal media results in slow growth and low final cell densities. Efficient agitation and aeration increase final cell densities. A skilled artisan will be able to determine which type of media is best suited to culture a particular species and/or strain of host cell.

Culturing or fermenting of host cells may be accomplished by any technique known in the art. In one aspect, batch fermentation can be conducted. In batch fermentation, the composition of the culture medium is set at the beginning of culturing and the system is closed to future artificial alterations. In some aspects, a limited form of batch fermentation can be carried out, wherein factors such as oxygen concentration and pH are manipulated, but additional carbon is not added. Continuous fermentation methods are also contemplated. In continuous fermentation, equal amounts of a defined medium are continuously added to and removed from a bioreactor. In other aspects, microbial host cells are immobilized on a substrate. Fermentation can be carried out on any scale and may include methods in which literal "fermentation" is carried out as well as other culture methods that are non-fermentative.

III. Methods for Enhancing the Physiological Properties of Plants

The selection of the plant used in the methods described herein can vary depending upon the application. For example, a specific plant can be selected that produces certain desirable metabolites. An example of one such metabolite is lycopene. Lycopene has numerous applications in the food industry (e.g., colorants and food enrichment), pharmaceuticals (e.g., anti-cancer agents), and cosmetics (e.g., anti-oxidants and skin-healing agents). Current techniques for producing lycopene are expensive. For example, lengthy and expensive synthetic procedures are required to produce lycopene on large scale. The biological devices and methods described herein enhance the production of lycopene from plants that naturally produce lycopene. In one aspect, the plant can include but is not limited to lulo or naranjillo (*Solanum quitoense*), tomatoes (*Solanum lycopersicum*), or carrots (*Daucus carota*).

In one aspect, plant cells when contacted with the biological devices described above exhibit enhanced production of lycopene. Recipient cell targets include, but are not limited to, meristem cells, Type I, Type II, and Type III callus, immature embryos and gametic cells such as microspores, pollen, sperm, and egg cells. It is contemplated that any cell from which a fertile plant may be regenerated is useful as a recipient cell. Type I, Type II, and Type III callus may be initiated from tissue sources including, but not limited to, immature embryos, immature inflorescenses, seedling apical meristems, microspores, and the like. Those cells that are capable of proliferating as callus also are also useful herein. Methods for growing plant cells are known in the art (see U.S. Pat. No. 7,919,679). Exemplary procedures for growing plant calluses are provided in the Examples. In one aspect, plant calluses grown from 2 to 4 weeks can be used herein. The plant cells can also be derived from plants varying in age. For example, plants that are 80 days to 120 days old after pollination can be used to produce calluses useful herein.

The plant cells can be contacted with the biological device in a number of different ways. In one aspect, the device can be added to a media containing the plant cells. In another aspect, the device can be injected into the plant cells via syringe. The amount of device and the duration of exposure to the device can vary as well. In one aspect, the concentration of the device is about $10^3$, $10^4$, $10^5$, $10^6$, $10^7$, $10^8$, or $10^9$ cells/mL of water. In one aspect, when the host cell is bacteria, the concentration of the device is $10^6$. In another aspect, when the host cell is yeast, the concentration of the device is $10^9$. Different volumes of the biological device can be used as well, ranging from 5 µL to 500 µL.

Once the plant cells have been in contact with the biological device for a sufficient time to produce the metabolite (e.g., lycopene), the metabolite is isolated. In one aspect, the metabolite is extracted from the media containing the biological device and the plant cells. The selection of the extraction solvent can vary depending upon the solubility of the metabolite. Exemplary procedures for extracting metabolites produced by the biological devices described herein are provided in the Examples.

With current techniques, the extraction of metabolites produced from plants usually requires high initial amounts of plant biomass or material, which in turn requires larger amounts of extractions solvents. The use of higher amounts of extractions solvents adds to the expense of lycopene production. The use of higher amounts of organic solvents presents environmental risks as well. However, the use of the biological devices described herein produces significantly higher amounts of metabolites such as lycopene, which means smaller amounts of biomass are required in order to produce and isolate the metabolites when compared with existing techniques. The extraction of plant metabolites using current techniques also requires fresh biomass, which entails agronomic practices, the use of chemicals, and time consuming extraction methods. Therefore, the use of the biological devices described herein is more cost-effective and safer for the environment than traditional methods for producing and synthesizing lycopene.

In other aspects, the devices and methods described herein can increase the growth rate of a plant. In particular, the devices and methods described herein are effective in accelerating plant development in the early stages of tissue culturing. By accelerating plant development in the early stages, it is possible to harvest more metabolites from the plant. Additionally, the devices and methods described herein protect plant tissue cultures against microbial contamination, which is a problem associated with tissue culturing. Finally, conventional methods for tissue culture involve the use of synthetic growth factors such as 2-4-D which can pose environmental concerns. The devices and methods described herein avoid the need for such compounds.

In certain aspects, any of the biological devices described above can be used in combination with a polysaccharide to enhance one or more physiological properties of the plant. In one aspect, the plant cells are first contacted with the biological device then subsequently contacted with the polysaccharide. In another aspect, the plant cells are first contacted with the polysaccharide then subsequently contacted with the biological device. In a further aspect, the plant cells are only contacted with a polysaccharide and not contacted with the biological device. In a still further aspect, the plant cells are contacted simultaneously with the polysaccharide and the biological device.

In one aspect, the polysaccharide includes chitosan, glucosamine (GlcN), N-acetylglucosamine (NAG), or any combination thereof. Chitosan is generally composed of glucosamine units and N-acetylglucosamine units and can be chemically or enzymatically extracted from chitin, which is a component of arthropod exoskeletons and fungal and microbial cell walls. In certain aspects, the chitosan can be acetylated to a specific degree of acetylation in order to enhance tissue growth during culturing as well as metabolite production. In one aspect, the chitosan is from 60% to about 100%, 70% to 90%, 75% to 85%, or about 80% acetylated. Exemplary procedures for producing and isolating the chitosan are provided in the Examples. In one aspect, chitosan isolated from the shells of crab, shrimp, lobster, and/or krill is useful herein.

The molecular weight of the chitosan can vary, as well. For example, the chitosan comprises about 3, 4, 5, 6, 7, 8, 9, 10, 11, 12, 13, 14, 15, 16, 17, 18, 19, or 20 glucosamine units and/or N-acetylglucosamine units. In another aspect, the chitosan includes 5 to 7 glucosamine units and/or N-acetylglucosamine units. In one aspect, the chitosan is in a solution of water and acetic acid at less than 1% by weight, less than 0.75% by weight, less than 0.50% by weight, less than 0.25% by weight, or less than 0.10% by weight. In another aspect, amount of chitosan that is applied to the plant cells is from 0.10% to 0.01% by weight, from 0.075% to 0.025% by weight, or is about 0.05% by weight. The polysaccharides used herein are generally natural polymers and thus present no environmental concerns. Additionally, the polysaccharide can be used in acceptably low concentrations. In certain aspects, the polysaccharide can be used in combination with one or more growth regulators.

In one aspect, the plant growth regulator is an auxin, a cytokinin, a gibberellin, abscisic acid, or a polyamine. In a further aspect, the auxin is a natural or synthetic auxin. In a still further aspect, the auxin is indole-3-acetic acid (IAA), 4-chloroindole-3-acetic acid (4-Cl-IAA), 2-phenylacetic acid (PAA), indole-3-butyric acid (IBA), 2,4-dichlorophenoxyacetic acid (2,4-D), α-naphthalene acetic acid (α-NAA), 2-methoxy-3,6-dichlorobenzoic acid (dicamba), 4-amino-3,5,6-trichloropicolinic acid (torden or picloram), 2,4,5-trichloropicolinic acid (2,4,5-T), or a combination thereof. In another aspect, the cytokinin is zeatin, kinetin, 6-benzylaminopurine, diphenylurea, thidizuron (TDZ), 6-(γ, γ-dimethylallylamino)purine, or a combination thereof. In another aspect, the gibberellin is gibberellin A1 (GA1), gibberellic acid (GA3), ent-gibberellane, ent-kaurene, or a combination thereof. In yet another aspect, the polyamine is putrescine, spermidine, or a combination thereof.

In one aspect, the plant cell or callus is first contacted with a polysaccharide and subsequently contacted with a plant growth regulator. In another aspect, the plant cell or callus is first contacted with a plant growth regulator and subsequently contacted with a polysaccharide. In an alternative aspect, the plant cell or callus is simultaneously contacted with a polysaccharide and a plant growth regulator. In a further aspect, the plant cell or callus is only contacted with a polysaccharide and is not contacted with a plant growth regulator.

The plant cells can be contacted with the polysaccharide using a number of techniques. In one aspect, the plant cells or reproductive organs (e.g., a plant embryo) can be cultured in agar and medium with a solution of the polysaccharide. In other aspects, the polysaccharide can be applied to a plant callus by techniques such as, for example, coating the callus or injecting the polysaccharide into the callus. In this aspect, the age of the callus can vary depending upon the type of plant. The amount of polysaccharide can vary depending upon, among other things, the selection and number of plant cells. The use of the polysaccharide in the methods described herein permit rapid tissue culturing at room temperature. Due to the ability of the polysaccharide to prevent microbial contamination, the tissue cultures can grow for extended periods of time ranging from days to several weeks. Moreover, tissue culturing with the polysaccharide can occur in the dark and/or light. As discussed above, the plant cells can optionally be contacted with any of the biological devices described above. Thus, the use of the polysaccharides and biological devices described herein is a versatile way to culture and grow plant cells—and, ultimately, plants of interest—with enhanced physiological properties.

In other aspects, the plant cells can be cultured in a liquid medium on a larger scale in a bioreactor. For example, plant cells can be cultured in agar and medium, then subsequently contacted with (e.g., injected) with a biological device described herein. After a sufficient culturing time (e.g., two to four weeks), the plant cells are introduced into a container with the same medium used above and, additionally, the polysaccharide. In certain aspects, the polysaccharide can be introduced with anionic polysaccharides including, but not limited to, alginates (e.g., sodium, calcium, potassium, etc.). After the introduction of the polysaccharide, the solution is mixed for a sufficient time to produce a desired result (e.g., production of a desired metabolite).

In one aspect, a method for increasing the production from lycopene involves
(a) contacting a plant callus with a device described herein;
(b) culturing the plant callus; and
(c) removing the lycopene from the plant callus.

In another aspect, a method for the production of lycopene is provided comprising:
(a) providing a recombinant microbial host cell comprising a DNA construct described herein;
(b) contacting a plant cell with the microbial host cell of (a);
(c) growing the plant cell of (b) for a sufficient time; and
(d) optionally recovering the lycopene.

In still another aspect, a method for the production of lycopene is provided comprising:
(a) providing a recombinant microbial host cell comprising a DNA construct described herein;
(b) contacting a plant cell with the microbial host cell of (a);
(c) optionally contacting the plant cell with a polysaccharide;
(d) growing the plant cell of (b) for s sufficient time; and
(e) optionally recovering the lycopene.

In one aspect, the plant callus is immersed in a solution of polysaccharide (e.g., chitosan) then inoculated with device. In one aspect, the plant callus is that of lulo or naranjillo (*Solanum quitoense*), tomato (*Solanum lycopersicum*), or carrot (*Daucus carota*). The plant callus can be from 2 days up to 20 days old prior to inoculation with the device. The plant callus is then allowed to grow until it is of sufficient weight and size. In one aspect, the plant callus is allowed to grow (i.e., culture) for 1 to 10 weeks after inoculation. The next step involves removal of the lycopene from the callus. In one aspect, the callus is macerated with a solvent to produce a macerate. The macerate is then extracted with a solvent to in order to remove lycopene. The extraction solvent is not a harsh solvent, and is generally environmentally friendly. In one aspect, the extraction solvent is ethyl acetate. Exemplary methods for producing calluses using the devices described herein and extractions of lycopene are provided in the Examples.

In one aspect, lycopene produced from a plant callus can be useful in pharmaceutical applications. Not wishing to be bound by theory, the lycopene produced from callus will have fewer impurities and thus will be easier to purify for pharmaceutical applications.

In another aspect, a plant callus described above can be planted and allowed to grow and mature into a plant bearing fruit and leaves. In one aspect, lycopene can be isolated from a plant that has been grown from a plant callus inoculated with a device described herein and optionally contacted with a polysaccharide (e.g., chitosan). In one aspect, lycopene can be removed from fruit or leaves of a plant grown with the devices described herein. In one aspect, the fruit and leaves of *Solanum quitoense* grown from calluses inoculated with the devices described herein provide a rich source of lycopene. Exemplary methods for isolating lycopene from the fruit and leaves of *Solanum quitoense* are provided in the Examples.

In one aspect, the fruits and leaves of plants grown with the assistance of the devices described herein can be useful in the production of a number of food products where the food product is enriched with lycopene. For example, juice from the fruit of *Solanum quitoense* will be enriched with lycopene. The leaves of *Solanum quitoense* can be ground up and consumed as a spice. In either case, the consumer is eating natural products with increased levels of lycopene, which provide health benefits. For example, the lycopene produced by the methods described herein can be incorporated in a number of cosmetic and skin care products.

In one aspect, the amount of lycopene produced by the plant cells, plant callus, and/or plants that have been contacted with the biological device as described herein is from 1.1 to 4-fold greater than the amount of lycopene produced by otherwise identical plant cells, plant callus, and/or plants that have not been contacted with the biological device as described herein.

The devices and methods described herein also enhance the growth rate of plants. For example, plants grown using the devices and methods described herein can be grown in 2 to 4 weeks versus the 32 weeks typically required for conventional field growth. Therefore, more plants can be harvested and, thus, more lycopene can be produced and isolated in a shorter period of time. Moreover, the devices and methods described herein do not require the use of synthetic chemicals and can be used in a closed environment and not in the field. Thus, the devices and methods described herein provide a versatile and cost-effective way to grow plants and produce desirable metabolites in significant quantities.

In another embodiment, the metabolite produced by the devices and methods described herein can be used to prevent the plant from contracting one or more diseases and/or to enhance the physical properties of the plant. For example, the metabolites can be used as antifungal agents.

In another aspect, the devices and methods described herein can enhance the production of lycopene when fermented in a culture medium. In one aspect, a vector comprising any of the DNA constructs described herein can be admixed with a culture medium comprising host cells. Upon transformation of the host cells with the DNA construct to produce the biological device, the biological device can be fermented for a sufficient amount of time to produce lycopene. The process can be performed at room temperature, and the pH of the culture medium including the host cell can vary as needed. The process can be performed using a batch pr continuous process.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such processes and conditions.

Plant Callus Treatment and Development

Different plants were tested to determine the effectiveness of the methods described herein. Somatic embryos, when used, were developed from mature and immature sexual embryos. The embryogenic potential varied with the organ and its maturity; however mature seeds gave better results for lulo or naranjillo (Solanum quitoense). A similar procedure was followed for tomato as for lulo/naranjillo.

Different sources of explants were used, including complete or segmented organs, roots, or hypocotyls. Healthy and vigorous plants were selected to be the sources of explants. Various plant tissues were used as explant sources; stems gave particularly good results. In the case where fruits were used as explants, fruits having different ages were used, including those that were 10, 20, 50, 80, and 120 days old. Older fruits, such as those of 80 and 120 days, were preferred.

Plant tissues were examined for pathogens such as viruses, bacteria, and fungi. When pathogens were found, various treatments were employed, including bactericides, fungicides, heat treatments, and/or quarantine.

In order to isolate the embryos, explants were planted in Petri dishes in culture medium composed of mineral salts and microelements of Murashige and Skoog (MS) medium with gellan gum (2.4 g/L) as a gelling agent. For lulo/naranjillo (Solanum quitoense), explant time during incubation was extended to two weeks, followed by a week with exposure to light. Different times for exposure were tested, ranging from 4 to 24 hours, with a 16-hour photoperiod as the preferred time. Samples were irradiated using a photon flux of 40 µmol/m$^2$·s. Similar procedures were followed with tomato plants, embryos, and calluses.

Preparation of DNA Construct

The DNA construct was composed of genetic components described herein and assembled in plasmid vectors (e.g., pYES and pBSKII). Sequences of genes and/or proteins with desired properties were identified in GenBank; these included a beta-carotene hydroxylase gene and a lycopene epsilon-cyclase gene. These sequences were synthesized by CloneTex Systems, Inc. (Austin, Tex.). Other genetic parts were also obtained for inclusion in the DNA constructs including, for example, promoter genes (e.g. T3 promoter), reporter genes (e.g. cyan fluorescent reporter protein), terminator sequences, and regulatory proteins (e.g. ribosomal binding site). These genetic parts included restriction sites for ease of insertion into plasmid vectors.

The cloning of the DNA construct into the biological devices was performed as follows. Sequences of individual genes were amplified by polymerase chain reaction using primers that incorporated restriction sites at their 5' ends to facilitate construction of the full sequence to be inserted into the plasmid. Genes were then ligated using standard protocols to form an insert. A pBSKII plasmid was then digested with HindIII restriction enzyme according to directions and using reagents provided by the enzyme's supplier (Promega). The complete insert, containing HindIII restriction sites on each end, was then ligated into the plasmid. Successful construction of the insert and ligation of the insert into the plasmid were confirmed by gel electrophoresis.

A schematic of the DNA construct is depicted in FIG. 1. From 5' to 3', the construct includes T3 promoter, a gene expressing beta-carotene hydroxylase, a gene expressing lycopene epsilon-cyclase, a ribosomal binding site, a cyan reporter protein, a terminator or stop sequence, a selective marker for ampicillin resistance, and a pUC origin. The DNA construct was incorporated into a pBSKII plasmid.

PCR was used to enhance DNA concentration using a Mastercycler Personal 5332 ThermoCycler (Eppendorf North America) with specific sequence primers and the standard method for amplification (Sambrook, J., E. F. Fritsch, and T. Maniatis. 1989. Molecular cloning: A Laboratory Manual, 2nd ed., vol. 1. Cold Spring Harbor Laboratory Press, Cold Spring Harbor, N.Y.). Digestion and ligation were used to ensure assembly of DNA synthesized parts using restriction enzymes and reagents (PCR master mix, restriction enzymes: XhoI, KpnI, XbaI EcoRI, BamHI and HindIII, alkaline phosphatase and quick ligation kit, all from Promega). DNA was quantified using a NanoVue spectrophotometer (GE Life Sciences) and a standard UV/visible spectrophotometer using the ratio of absorbances at 260 nm versus 280 nm. In order to verify final ligations, DNA was visualized and purified via electrophoresis using a Thermo EC-150 power supply.

The DNA construct was made with gene parts having sequence sizes ranging from 30 to 1000 bp, including gene parts fundamental for expression of such as, for example, ribosomal biding sites, native and constitutive promoters, reporter genes, and transcriptional terminators or stops. Backbone plasmids and synthetic inserts can be mixed together for ligation purposes at different ratios ranging from 1:1, 1:2, 1:3, 1:4, and up to 1:5. In one aspect, the ratio of backbone plasmid to synthetic insert is 1:4. After the vector comprising the DNA construct has been produced, the resulting vector can be incorporated into the host cells using the methods described below.

The DNA device for the production of lycopene was constructed by assembling a plasmid (pBSKII) having the genetic components in the following order: (1) T3 promoter (SEQ ID NO. 1), (2) a gene that expresses beta-carotene hydroxylase (343 bps), (3) a gene that expresses lycopene epsilon-cyclase (SEQ ID NO. 4), (3) ribosomal binding site (SEQ ID NO. 11), and (4) a terminator (SEQ ID NO. 13). In certain embodiments, the reporter protein (SEQ ID NO. 14) that produces fluorescence can be incorporated into the plasmid prior to the terminator from the 5' to 3' direction. The amount of fluorescence correlates to metabolite production in tissues and media. The DNA construct was transformed into cells, as described below, to produce the biological devices. A plasmid containing the DNA construct is shown in FIG. 1.

Host Cell Purification and Transformation

Established laboratory procedures were followed for yeast transformations (Gietz, R. D. and R. H. Schiestl. 2007. Nature Protocols. Quick and easy yeast transformation using the LiAc/SS carrier DNA/PEG method. Vol 2., 35-37. doi: 10.1038/nprot.2007.14).

Yeast (Saccharomyces cerevisiae ATCC 200892) or bacterial cells such as Escherichia coli (using TOP10 and/or DH10B™ chemically competent cells from Life Technologies™) or *Bacillus pumilus* (ATCC 8471) were transformed with the DNA construct. Host cells were in some cases isolated as entophytes from fruits and plant tissues. Fruits and plant tissues were disinfected under full aseptic conditions in a laminar flow cabinet and placed in a solution of ethanol (70%) for two minutes, then in sodium hypochlorite (5%) for two minutes, then rinsed three times with sterile distilled water. Dilutions of disinfected samples and slices of samples were placed in different selective and non-selective media for bacteria and yeast and placed under anaerobic or aerobic conditions. After incubation, different bacteria and yeast were isolated. After pathogenesis assays, the cells that were less pathogenic as well as possessing better growth rates and exempt from disease were selected as ideal host cells for plant tissue induction. Cells selected were identified using ribosomal RNA gene sequencing. Identified bacteria were purchased from ATCC.

Transformation proceeded according to manufacturers' protocols. In the case of *E. coli*, chemical transformation was performed. The yeast devices were transformed and made competent by the methods disclosed in Gietz, R. D. & R. H. Schiestl, 2007. *Bacillus pumilus* transformation was accomplished by electroporation of competent cells using 1.25 V/mm for 3.9 seconds and recovering the cells with 1 ml of thioglycolate broth enriched with 250 mM sucrose, 1 mM $MgCl_2$, and 5 mM $MgSO_4$ for an hour at 30° C. and plated on Muller Hilton agar with ampicillin Cells were made competent by a new chemical treatment preparation with an electroporation buffer containing 0.5 M HEPES, 0.5 M sucrose, glycerol at 80%, and 25 mM of $MgCl_2$. The buffer was added to pelleted cells after overnight growth in aseptic conditions at a temperature of 4° C. The pellet was centrifuged and washed three times with the buffer, aliquotted, and used immediately or stored at −80° C.

DNA expression and effectiveness of transformation were determined by fluorescence of the transformed cells expressed in fluorescence units (FSUs), according a protocol provided by the manufacturer, using a 20/20 Luminometer (Promega). The blue fluorescence module using a 450 nm excitation wavelength and a 600 nm emission wavelength was used to evaluate the effectiveness of transformation. Plasmid DNA extraction purification, PCR, and gel electrophoresis were also used to confirm transformation.

Different transformed devices were obtained. Different types of fluorescent reporter proteins were used (yellow fluorescent protein, red fluorescent protein, green fluorescent protein, and cyan fluorescent protein) for all transformed cells or devices. However, the cyan fluorescent protein was preferred. When no fluorescent reporter protein was assembled, no fluorescence was observed.

Calluses

Production of plant calluses and growth of the plants *Solanum quitoense* and *Solanum lycopersicum* for lycopene production was performed following standard procedures developed by Murashige and Skoog ("A revised medium for rapid growth and bio-assay with tobacco tissues," 1962, *Physiol. Plant,* 15(3): 473-497).

Chitosan

Chitosan is a natural linear polysaccharide compound composed of randomly distributed β-(1-4)-linked D-glucosamine and N-acetyl-D-glucosamine residues. To produce chitosan, chitin was first extracted from the exoskeletons of crustaceans (e.g., shrimp and/or crabs). Samples were treated variously with inorganic acid (to demineralize), sodium hydroxide (to remove proteins), and organic solvents (to remove lipids and other hydrophobic components). Chitin was deacetylated to produce chitosan (degree of acetylation approximately 70-80%), again using sodium hydroxide. Here, the chitosan was dissolved in glacial acetic acid and used as a concentrate of 1%.

In Vitro Assays

Callus derived from somatic embryogenesis was sown on MS medium. The MS medium was prepared as follows: to 200 mL of distilled water were added 4.3 g MS salt mixture, 2 mL of growth regulator 2,4-D, 5 mL of myo-inositol (100 mg/L), and 30 g of sucrose to produce a first medium. In a separate container, 2.4 g of agar was added to 800 mL of distilled water in order to completely dilute the agar. This was added to the contents of the first medium, mixed while boiling, and autoclaved at 121° C. for 20 minutes at 15 psi above atmospheric pressure.

To this medium was added a stock solution of chitosan to achieve a chitosan concentration of 0.01%, 0.05%, 0.1%, or 0.5%. The pH was adjusted with a solution of 1 M NaOH. The media was served in disposable sterile plastic petri dishes and calluses were subcultured.

The DNA construct transformed in different host cells were replicated overnight in Luria Brethani (LB) broth and Yeast extract-peptone-D-glucose (YPD) broth with ampicillin to produce the biological device. Serial dilutions of these cultures were made until reaching a dilution of $10^9$ cells/mL in sterile water to a final volume of 5 mL. Dilutions of $10^3$, $10^6$, and $10^9$ were used for all devices; however, using more concentrated solutions was preferable. The number of cells of each dilution was calculated with a standard growth curve of absorbance vs. Colony Forming Units (CFU), to ensure the concentration of cells used in each of the dilutions. Absorbance was measured with a standard UV/visible spectrophotometer between 520 and 600 nm For the inoculation process, different volumes of the biological device were tested to standardize the amount necessary to induce metabolite production and avoid plant damage including 0.1, 0.25, 0.3, 0.5, 0.7, 0.9, 1.0, and 1.25 mL of device. 0.25 mL was the preferred volume, as it showed better induction results; therefore, 0.25 mL of the device was prepared at a concentration of $1\times10^3$ cells/mL from solutions containing $10^9$ and $10^{10}$ cells. The device was added to the callus a number of ways including adding the device to the media containing the callus via a micropipette or, in the alternative, injecting the device into the callus with a thin syringe.

Sample treatment depended on the type of plant tissue culture, the number and type of DNA and host cells, and the metabolite or other type of induction expected. Control treatment was plant tissue culture alone without any device inoculation or chitosan. Plant tissue culture alone without any device inoculation but with chitosan added to the media was evaluated. Device treatments with and without chitosan were evaluated. At the same time, 3 different dilutions of each device were evaluated giving a total of 8 treatments per assay. When more than one device was evaluated, the number of treatments increased. For each treatment, 3 replicates with 3 and 4 calluses per replicate were used giving a total of 12 calluses per treatment. Samples were incubated at 25° C. with stirring at 50 rpm in the dark.

A daily record was made taking into account the following variables: callus size, germination structures, callus color, and media color. Gene expression was monitored by techniques including RNA concentration, DNA concentration, and fluorescence (in case of devices containing protein reporter gene).

From the fourth day, differences in morphology were visible. Size, callus coloration, and media color also changed. In the case of inoculations with devices that induce this type of visible change, secondary metabolites are released into the media. On the other hand, for samples in which there was no phenotypic difference, the samples were collected for chemical extraction and analysis of produced compounds. For lycopene content analysis, the Folin-Ciocalteu method and HPLC were used to determine metabolite presence and concentration.

Production of Lycopene from *Solanum quitoense* (Experiment 1)

Table 1 summarizes the results of using the methods described herein for producing lycopene from naranjillo (*Solanum quitoense*) using yeast host cells transformed with the DNA construct (i.e., the lycopene device). The results show a significant increase in lycopene production when the lycopene device is used in combination with chitosan.

TABLE 1

Concentration of lycopene extracted from naranjillo (*Solanum quitoense*) seedlings treated and non-treated (control) with transformed yeast and/or chitosan addition, determined after Soxhlet extraction using UV/Vis spectrophotometry. The difference in concentrations shows the induction of lycopene by chitosan and lycopene device.

| Treatment | Concentration (mg/L) | SD |
|---|---|---|
| treated with lycopene device + chitosan | 0.1912 | 0.0024 |
| treated with lycopene device | 0.0401 | 0.0000 |
| treated with chitosan | 0.0261 | 0.0006 |
| treated with water: control | 0.0113 | 0.0000 |

In another experiment, the following procedure was used to prepare and quantify lycopene compounds using the lycopene device.

1. Obtain the wet weight of the biomass (plant 15 days old).
2. Take the sample (callus) and add 500 μL of 70% ethanol then macerate.
3. Add 500 μl of olive oil. Mix for 15 minutes in a water bath at 60° C. until it homogenizes.
4. Take the homogeneous sample to a funnel.
5. Discard the white serum obtained from decantation and storage the lycopene-rich solution at 8° C.

6. The lycopene percentage was obtained with the formula:

$$\% = \frac{Conc. \text{ of the sample at 400 nm (mg/L)} \times Vol. \text{ of the working } sln. (L) \times \text{Dilution factor} \times 100}{\text{Sample weight (mg)}}$$

From the formula above, the concentration of lycopene is (mg/L):

$$\frac{\text{lycopene percentage} \times \text{Sample weight (mg)}}{100 \times Vol. \text{ of the working } sln. (L) \times \text{Dilution factor}}$$

7. Quantification of ppm of lycopene in UV visible spectrophotometer at 400 nm. Sample diluted in hexane. Blank used: hexane.

Based on the results in Table 2, results it was observed that at the two weeks of experimental assembly for the lulo plant callus, the treatment that presented the major concentration of lycopene was the plant callus inoculated with the lycopene device (15.1 mg/L), followed by the treatment of the plant with chitosan and subsequent inoculation with the lycopene device (10.1 mg/L). The treatment of the control and chitosan presented similar values.

TABLE 2

Lycopene concentrations obtained from the extraction of plant callus of *Solanum quitoense* Lam by the direct solubilization method using different treatments.

|  | 2 weeks | | | 1 month | | |
|---|---|---|---|---|---|---|
|  | Callus | mg/L of lycopene | | Callus | mg/L of lycopene | |
| Treatment | weight (g) | Average | Standard deviation | weight (g) | Average | Standard deviation |
| Control (1) | 1 | 8.90 | 0.83 | 1 | 17.72 | 0.77 |
| Chitosan (2) | 1 | 9.29 | 0.55 | 1 | 24.47 | 0.54 |
| Lycopene device (3) | 1 | 15.12 | 0.58 | 1 | 23.04 | 0.87 |
| Device + Chitosan (4) | 1 | 10.09 | 0.44 | 1 | 18.60 | 0.60 |

(1) Plant callus biomass of *Solanum quitoense* Lam
(2) Plant callus biomass of *Solanum quitoense* Lam submerged in 0.01% chitosan for 5 minutes.
(3) Plant callus biomass of *Solanum quitoense* Lam inoculated with lycopene device.
(4) Plant callus biomass of *Solanum quitoense* Lam submerged in 0.01% chitosan for 5 minutes, and inoculated with lycopene device.

Figure 2:
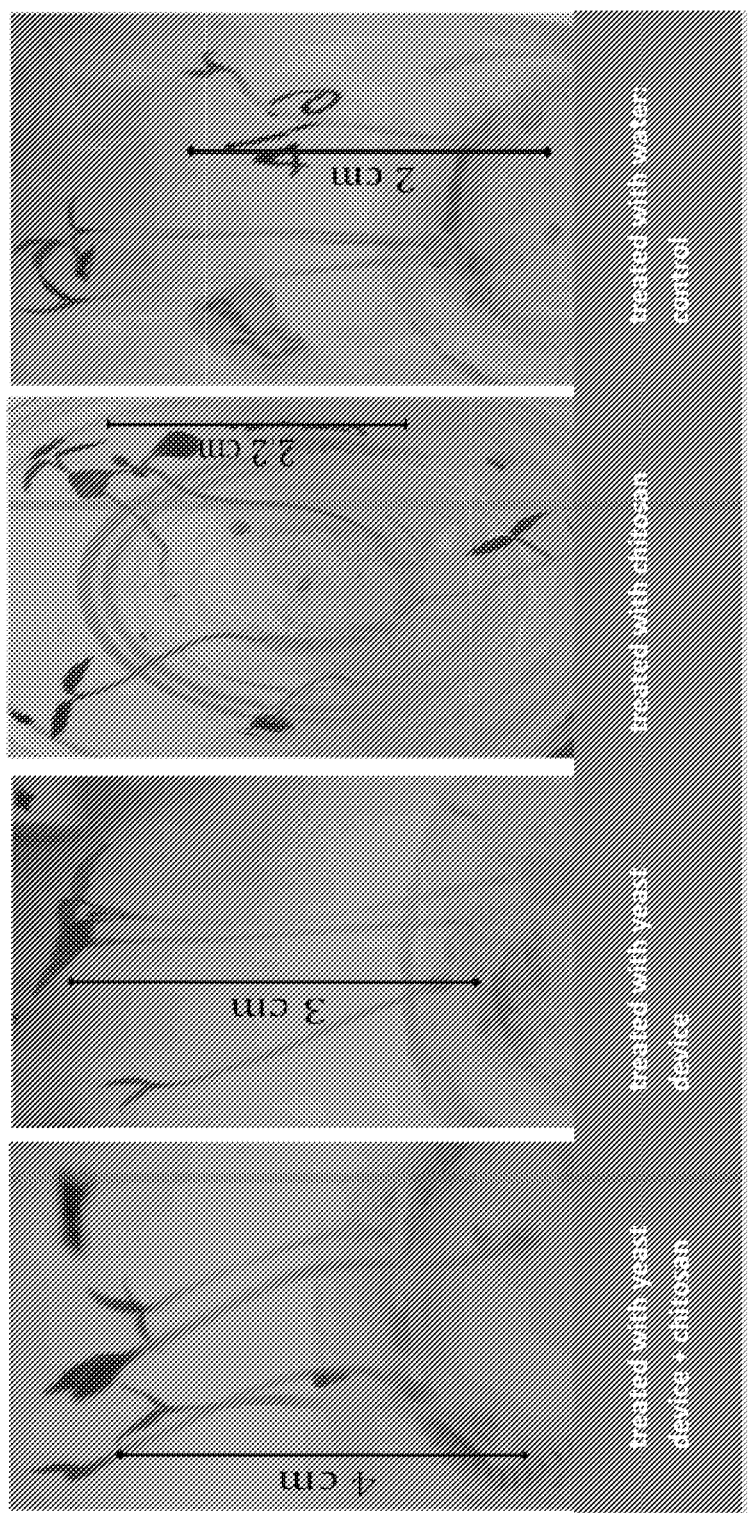
FIG. 2 shows embryonic plant seedlings from callus tissue of naranjillo (*Solanum quitoense*) in culture media after 10 days. The difference in embryo and foliar development is shown for seedlings treated and non-treated (control) with transformed yeast and/or chitosan addition. Seedlings treated with the lycopene device and chitosan had a height of 3.5 to 4 cm; seedlings treated with the lycopene device had a height of 3 to 4 cm; seedlings treated with chitosan had a height of 2.2 to 3 cm; control seedlings treated with water had a height of 0.5 to 2 cm.

FIG. 2 shows embryogenic plant seedlings from callus of naranjillo (*Solanum quitoense*) in culture media after 10 days. The difference in embryo and foliar development is shown for seedlings treated and non-treated (control) with the lycopene device and/or chitosan addition. Seedlings treated with the lycopene device and chitosan had a height of 3.5 to 4 cm; seedlings treated with the lycopene device had a height of 3 to 4 cm; seedlings treated with chitosan had a height of 2.2 to 3 cm; control seedlings treated with water had a height of 0.5 to 2 cm.

Production of Lycopene from *Solanum quitoense* (Experiment 2)

15-day-old calluses were inoculated as described previously. These were then placed in an environmental chamber under continued white light. After four weeks, these calluses were transferred to trays with fresh nutrients. During this time, the calluses were sprayed with water daily. Every two weeks, they were also sprayed with fresh nutrients (MS medium) and/or chitosan at different concentrations such as 0.0001, 0.0002, 0.0005, 0.001, 0.002, 0.005, 0.01, 0.02, 0.05, or 0.1%.

After three months of growth in trays, the small plants were transferred to plastic bags containing sterilized soil with nutrients. During this period, the small plants were sprayed with water daily and sprayed with fresh nutrients every two weeks.

a. Experimental Treatment of Callus Tissue

Calluses exhibiting initial root or leaf formation were preferred for inoculation with the DNA devices described herein. Calluses were separated into the following four treatment groups:
1. Control: Calluses without any treatment were immersed in water for 5 min
2. Chitosan treatment: Calluses were immersed for 1, 2, 3, 5, 10, 15, 20, or 30 min in a chitosan solution at 0.01, 0.02, 0.05, 0.1, 0.2, 0.5, 0.7, or 1% concentration. 0.05% chitosan treatment for 5 min was particularly effective.
3. DNA device treatment: Calluses were inoculated with $10^3$, $10^4$, $10^6$, or $10^9$ cells/mL of cells containing the DNA device described herein. Different volumes of bacterial or yeast cells were used herein, including 3, 5, 10, 15, 25, 50, or 60 µL, with 5 µL being especially effective for calluses that weighed less than 1 g, while 5 µL to 10 µL was effective for calluses weighing more than 1 g.
4. Chitosan+DNA device treatment: Calluses were immersed in chitosan as described in item 2 above, followed by inoculation with transformed cells containing the DNA device as described in item 3 above.

b. Extraction of Lycopene from *Solanum quitoense* Using Direct Solubilization with Oil
1. Calluses were weighted based on their wet biomass.
2. Weighed calluses were freeze-dried (lyophilization) at −40° C. for 24 h.
3. Calluses were weighed again based on dry biomass.
4. Calluses were then macerated and pulverized using 70% ethanol. 300 µL to 700 µL of ethanol was mixed with each single sample of calluses, with 500 µL of ethanol preferred.
5. 500 µL to 700 µL of olive oil were added, with 500 µL of olive oil were preferred. Samples were then subjected to hot bath (60° C.) for 15 minutes. Samples were also homogenized during the process.
6. The supernatant contained the oily phase. This phase was dissolved in hexane at different ratios (hexane:supernatant of 1:1, 2:1, 3:1, 2:2, 4:1), but this varied according the concentration of the oily supernatant phase. Then, the concentration of lycopene was determined as follows:

Concentration of lycopene on percentage was determined by the following formula:

$$\% = \frac{\text{Sample } Conc. \text{ at } 400 \text{ nm (mg/L)} \times \text{Total working } Vol \text{ (L)} \times \text{Dilution Factor} \times 100}{\text{Sample Weight (mg)}}$$

Lycopene concentration (mg/L) was calculated from the formula above:

$$\frac{\text{Percentage of lycopene} \times \text{weight of simple (mg)}}{100 \times \text{Total Working } Vol. \text{ (L)} \times \text{Dilution factor}}$$

7. The, the final concentration in ppm was determined after subjecting the samples to spectrophotometric measurement at 400 nm in a UV-visible spectrophotometer Table 3 shows that after 2 weeks of treatment, the device alone and the composition of device+chitosan induced the higher (15.1 mg/L) lycopene production, as compared to calluses without treatment and just chitosan alone.

TABLE 3

Lycopene Production from Calluses of Naranjillo (*Solanum quitoense* Lam), using the olive oil extraction method

| | Week 2 | | | Week 4 | | |
|---|---|---|---|---|---|---|
| | Weight callus | mg/L lycopene | | Weight callus | mg/L lycopene | |
| TREATMENTS | (g) | Mean | ±SD | (g) | Mean | ±SD |
| Control (1) | 1 | 8.90 | 0.83 | 1 | 17.72 | 0.77 |
| Chitosan (2) | 1 | 9.29 | 0.55 | 1 | 24.47 | 0.54 |
| Device of lycopene (3) | 1 | 15.12 | 0.58 | 1 | 23.04 | 0.87 |
| Device + Chitosan (4) | 1 | 10.09 | 0.44 | 1 | 18.60 | 0.60 | c. Extraction of Lycopene Using Ethyl Acetate

Extraction of lycopene from plant tissues was performed according to the methodology developed by Cardona and Restrepo (Cardona, E. M. et al., "Extraction of the carotenoid lycopene from chonto tomato (*Lycopersicum esculentum*)," *Vitae: The Official Publication of the Faculty of Pharmaceutical Chemistry at the University of Antioquia*, 13(2), 2006, 44-53). Briefly, samples were weighed, macerated with ethyl acetate, and covered with aluminum foil. Samples were incubated in a 50° C. bath for 3 h with constant shaking at 350-500 rpm. Following incubation, samples were stored in the dark at room temperature.

Extraction of Lycopene from Callus

Callus samples were lyophilized for 12 hours prior to being weighed. For each treatment, 3-6 callus replicates were used each time. Ethyl acetate was added to samples at a ratio of 1:100 callus:ethyl acetate (w/v) and samples were macerated. Homogenized callus samples were sealed in glass containers and placed in a water bath with shaking as described above.

Extraction of Lycopene from Fruits

Pieces of fruits were weighed, then macerated and homogenized in ethyl acetate at a ratio of 1:4 of fruit:solvent (w/v). Homogenized samples were sealed in containers and placed in a water bath with shaking as described above.

Extraction of Lycopene from Leaves

Leaves were weighed, then macerated and homogenized in ethyl acetate at a ratio of 1:10 of leaf:solvent (w/v). Homogenized samples were sealed in containers and placed in a water bath with shaking as described above.

d. Production of Lycopene in Different Plant Tissues

Lycopene was extracted from *Solanum quitoense* callus after 4 weeks and after 8 weeks of treatment with chitosan and/or the DNA device described herein, from mature fruit samples (collected from 13-month-old plants), and from leaf samples (also collected from 13-month-old plants).

Various treatments of naranjillo callus were performed. These included: chitosan at 0.05%, the DNA device at $10^8$, the DNA device at $10^9$, the DNA device at $10^6$+0.05% chitosan, the DNA device at $10^8$+0.05% chitosan, and the DNA device at $10^9$+0.05% chitosan. Results from the most successful treatment of callus after 4 weeks are summarized in Table 4; lycopene was extracted using the olive oil method described above.

TABLE 4

Production of lycopene in naranjillo callus after 4 weeks' treatment

| Naranjillo callus after 4 weeks of treatment | Concentration of lycopene extracted (mg/100 g callus) |
|---|---|
| Callus without treatment (control) | 1989 ± 311.1 |
| Callus treated with device at $10^6$ cells/mL | 2529 ± 59.2 |
| % increase in lycopene | 27% |

The preceding treatments were also carried out on naranjillo callus for 8 weeks. Results from the most successful treatment are summarized in Table 5. Lycopene was extracted using ethyl acetate as described above.

TABLE 5

Production of lycopene in naranjillo callus after 8 weeks' treatment

| Naranjillo callus after 8 weeks of treatment | Concentration of lycopene extracted (mg/100 g callus) |
|---|---|
| Callus without treatment (control) | 7215 ± 369.09 |
| Callus treated with device at $10^6$ cells/mL | 9084 ± 670.06 |
| % increase in lycopene | 26% |

Multiple treatments were performed on mature fruits harvested from 13-month-old naranjillo plants. Results from the most successful treatment are summarized in Table 6. Lycopene was extracted using ethyl acetate as described above.

TABLE 6

Production of lycopene in mature fruits of naranjillo plants

| Mature fruits from naranjillo | Concentration of lycopene extracted (mg/100 g fruit) |
|---|---|
| Untreated naranjillo fruits (control) | 773 ± 7.6 |
| Fruits from plants treated with the DNA device at $10^{10}$ cells/mL + 0.05% chitosan | 1102 ± 3.5 |
| % increase in lycopene | 43% |

Multiple treatments were performed on mature fruits harvested from 13-month-old naranjillo plants. Results from the most successful treatment are summarized in Table 7. Lycopene was extracted using ethyl acetate as described above.

TABLE 7

Production of lycopene in green naranjillo leaves

| Leaves from 13-week-old naranjillo plants | Concentration of lycopene extracted (mg/100 g leaves) |
|---|---|
| Untreated naranjillo leaves | 884 ± 1.9 |
| Leaves treated with the DNA device at $10^{10}$ cells/mL + 0.05% chitosan | 3331 ± 18.8 |
| % increase in lycopene | 277% |

Production of Lycopene from *Solanum lycopersicum* (Experiment 3)

Lycopene production by tomato (*Solanum lycopersicum*) callus was assessed following the procedure for lulo or naranjillo callus. Callus samples with approximately 9 mg mass were grown for two weeks, then treated with the biological devices and/or polysaccharides described previously. Lycopene extraction was performed as previously described for lulo or naranjillo callus.

The following treatments were used to treat the calluses: 0.05% chitosan alone, device ($10^6$ cells/mL), device ($10^6$ cells/mL)+0.05% chitosan, device ($10^8$ cells/mL), device ($10^8$ cells/mL)+0.05% chitosan, device ($10^9$ cells/mL), and device ($10^9$ cells/mL)+0.05% chitosan. Results from the most successful treatments are provided in Table 8.

TABLE 8

Increase in Lycopene Production by Tomato Callus

| Treatment | mg lycopene per 100 g of tomato callus | % Increase in lycopene as compared to control |
|---|---|---|
| Control | 628.74 ± 20.76 | |
| Device ($10^6$ cells/mL) | 1885.58 ± 811.82 | 199 |
| Device ($10^9$ cells/mL) | 2204.56 ± 642.45 | 250 |
| Device ($10^9$ cells/mL) + chitosan (0.05%) | 3138 ± 773.40 | 399 |

Production of Lycopene from Tomato (Experiment 4)

Lycopene production by tomato (*Solanum lycopersicum*) callus was assessed following the procedure for lulo or naranjillo callus. Callus samples treated with and without the device were grown for two and four weeks. Lycopene extraction was performed as previously described for lulo or naranjillo callus. Results from the most successful treatments are provided in Table 9. The results indicate the lycopene device significantly increases the production of lycopene in tomato callus.

TABLE 9

Increase in Lycopene Production by Tomato Callus

| Treatment | 2 weeks mg lycopene/100 g tomato callus | 4 weeks mg lycopene/100 g tomato callus |
|---|---|---|
| CONTROL-Callus alone (no device) | 890.6 | 1,708.1 |
| Callus + DEVICE $10^9$ | 1,384.3 | 3,358.8 |

Production of Lycopene by Liquid Fermentation (Experiment 5)

The lycopene device used above was fermented in the culture medium in Table 10. The concentration of the device was 0.8 optical density at 600 nm

TABLE 10

| Ingredients | Grams/Liter |
|---|---|
| Peptic Digest of Animal Tissue | 5.0 |
| Yeast Extract | 3.0 |
| Malt Extract | 3.0 |
| Dextrose | 10.0 |
| Final pH 6.2 +/− 0.2 at 25° C. | |

To the culture medium above was added a solution of the lycopene device. The concentration of the device was 0.8 optical density at 600 nm. The concentration of lycopene was determined at 0, 24, 48, 72, and 96 hours at 25° C. The highest concentration of lycopene was observed at 48 hours. The results are shown in Table 11.

TABLE 11

| Treatments | (48 Hour) | |
|---|---|---|
| | O.D | Lycopene Production mg/100 g sample |
| 800 mL of culture medium + 1 mL of device solution. | 2.3 ± SD 0.02 | 1,747.2 ± SD 250.43 |
| 800 mL culture medium + 5 mL of device solution | 2.22 ± SD 0.01 | 1,832.7 ± SD 238.67 |

The production of lycopene by liquid fermentation was even higher than the highest production of lycopene in mature fruits (10-11 months old) of naranjillo (*Solanum quitoensi* at 592.1 mg/100 g of fruit biomass), which was originally treated with the device at callus stage. The concentration of the device at 48 hour was 2.2 optical density at 600 nm Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed:

1. A DNA construct comprising (a) a gene that expresses beta-carotene hydroxylase and (b) a gene that expresses lycopene epsilon-cyclase, wherein the gene that expresses beta-carotene hydroxylase is SEQ ID NO. 5 and the gene that expresses lycopene epsilon-cyclase is SEQ ID NO. 8.

2. The DNA construct of claim 1, further comprising a promoter.

3. The DNA construct of claim 2, wherein the promoter is a T3 promoter.

4. The construct of claim 3, wherein the T3 promoter is SEQ ID NOS. 1 or 2.

5. The construct of claim 1, further comprising a ribosomal binding site.

6. The construct of claim 5, wherein the ribosomal binding site has SEQ ID NOS. 11, 12, or a sequence having at least 90% homology thereof.

7. The construct of claim 1, further comprising a terminator.

8. The construct of claim 1, wherein the construct further comprises a gene that confers resistance to an antibiotic.

9. The construct of claim 1, wherein the DNA construct comprises the following components from 5' to 3' in the following sequence: a promoter, a gene that expresses beta-carotene hydroxylase having SEQ ID NO. 5, a gene that expresses lycopene epsilon-cyclase having SEQ ID NO. 8, a ribosomal binding site, and a terminator.

10. A vector comprising the construct of claim 1.

11. A biological device comprising host cells transformed with the DNA construct of claim 1.

12. The device of claim 11, wherein the host cells comprise yeast or bacteria.

13. A method for producing lycopene from plant cells, the method comprising contacting the plant cells with a biological device of claim 11.

14. The method of claim 13, wherein the plant cells comprise meristem cells, callus cells, immature embryos, gametic cells, or any combination thereof.

15. The method of claim 13, wherein the plant cells are derived from lulo or naranjillo (*Solanum quitoense*), tomatoes (*Solanum lycopersicum*), or carrots (*Daucus carota*).

16. The method of claim 13, wherein the plant cells are further contacted with chitosan.

17. The method of claim 16, wherein the chitosan is from 60% to 100% acetylated and has from 3 to 20 glucosamine units and/or N-acetylglucosamine units.

18. A method for preventing a plant from contracting one or more diseases, the method comprising growing a plant from plant cells that have been contacted with the device of claim 11.

19. A method for enhancing the growth of a plant, the method comprising growing a plant from plant cells that have been contacted with the device of claim 11.

20. The construct of claim 1, wherein the construct comprises from 5' to 3' the following genetic components in the following order: (a) the gene that expresses beta-carotene hydroxylase and (b) the gene that expresses lycopene epsilon-cyclase.

21. The vector of claim 10, wherein the vector is pBSK, pBSKII, pYES, or pYES2.

* * * * *

SEQUENCE LISTING

```
<160> NUMBER OF SEQ ID NOS: 13

<210> SEQ ID NO 1
<211> LENGTH: 23
<212> TYPE: DNA
<213> ORGANISM: Artificial Sequence
<220> FEATURE:
<223> OTHER INFORMATION: Synthetic Construct

<400> SEQUENCE: 1
aattaaccct cactaaaggg aga                                                23

<210> SEQ ID NO 2
<211> LENGTH: 17
<212> TYPE: DNA
<213> ORGANISM: Artificial Sequence
<220> FEATURE:
<223> OTHER INFORMATION: Synthetic Construct

<400> SEQUENCE: 2
attaaccctc actaaag                                                       17

<210> SEQ ID NO 3
<211> LENGTH: 46
<212> TYPE: DNA
<213> ORGANISM: Artificial Sequence
<220> FEATURE:
<223> OTHER INFORMATION: Synthetic Construct

<400> SEQUENCE: 3
taatacgact cactataggg aatacaagct acttgttctt tttgca                       46

<210> SEQ ID NO 4
<211> LENGTH: 1501
<212> TYPE: DNA
<213> ORGANISM: Artificial Sequence
<220> FEATURE:
<223> OTHER INFORMATION: Synthetic Construct

<400> SEQUENCE: 4
ttaaaacaag aagagggttg actacatcac gatgaggggg atcgaagaaa tgatggtaaa        60
tgaaatagga aatcaaggag catgaaggca aaagacaaat ataagggtcg aacgaaaaat       120
aaagtgaaaa gtgttgatat gatgtatttg gctttgcggc gccgaaaaaa cgagtttacg       180
caattgcaca atcatgctga ctctgtggcg gacccgcgct cttgccggcc cggcgataac       240
gctgggcgtg aggctgtgcc cggcggagtt ttttgcgcct gcattttcca aggtttaccc       300
```

```
tgcgctaagg ggcgagattg gagaagcaat aagaatgccg gttggggttg cgatgatgac      360
gaccacgaca actggtgtca ttatttaagt tgccgaaaga acctgagtgc atttgcaaca      420
tgagtatact agaagaatga gccaagactt gcgagacgcg agtttgccgg tggtgcgaac      480
aatagagcga ccatgacctt gaaggtgaga cgcgcataac cgctagagta ctttgaagag      540
gaaacagcaa tagggttgct accagtataa atagacaggt acatacaaca ctggaaatgg      600
ttgtctgttt gagtacgctt tcaattcatt tgggtgtgca cttttattatg ttacaatatg      660 gaagggaact ttacacttct cctatgcaca tatattaatt aaagtccaat gctagtagag      720 aagggggta acacccctcc gcgctctttt ccgattttt tctaaaccgt ggaatatttc       780
ggatatcctt tgttgtttc cgggtgtaca atatggactt cctctttct ggcaaccaaa       840 cccatacatc gggattccta taataccttc gttggtctcc ctaacatgta ggtggcggag      900
gggagatata caatagaaca gataccagac aagacataat gggctaaaca agactacacc      960
aattacactg cctcattgat ggtggtacat aacgaactaa tactgtagcc ctagacttga     1020
tagccatcat catatcgaag tttcactacc cttttccat ttgccatcta ttgaagtaat      1080
aataggcgca tgcaacttct tttcttttt tttcttttct ctctccccg ttgttgtctc      1140 accatatccg caatgacaaa aaaatgatgg aagacactaa aggaaaaaat taacgacaaa     1200
gacagcacca acagatgtcg ttgttccaga gctgatgagg ggtatctcga agcacacgaa     1260
actttttcct tccttcattc acgcacacta ctctctaatg agcaacggta tacggccttc     1320
cttccagtta cttgaatttg aaataaaaaa aagtttgctg tcttgctatc aagtataaat     1380
agacctgcaa ttattaatct tttgtttcct cgtcattgtt ctcgttccct ttcttccttg     1440 tttcttttc tgcacaatat ttcaagctat accaagcata caatcaacta tctcatatac     1500
a                                                                    1501

<210> SEQ ID NO 5
<211> LENGTH: 1030
<212> TYPE: DNA
<213> ORGANISM: Synechococcus sp.

<400> SEQUENCE: 5
atgacccaga gttctgcttt acatcagcaa ccaagaccag tatccacagg ctataggtct       60
gttcccagag agttcgttga tcctcctcct gcatggaatc ccaccgttgc tttgttcttg      120
ggaggatatg gcttagccgc ttttactatt tggggttggt tcttgggtgg tttgccctta      180
ccagtattat tgtgcactgg attcttggct ttacatttgg aaggtactgt gattcatgac      240
gcatgtcata acgctgctca tcctaatagg tggttaaatc aagccatggg tcatggaagt      300
gctttgttgt taggattctc tttccccgtt tcactagag tgcacttgga gcatcatgct      360
cacgtcaatg accccaagaa cgacccagat catattgttt caacttttgg cccattgtgg      420
ttaattgccc ctagattctt ttatcacgaa tggttcttct ttcagaggag attatggagg      480
aggtgggaat tgatgcaatg gggattggag agatccgtat ttgtggtcat tgtattatct      540
gcagcaagat ttgagttctt gccattcatt ttcaactgtt ggtttgctcc tgcattgatg      600
gtcggtgtga ctttaggttt gttctttgat tacttgccac ataggccatt tacatcaaga      660
aatagatgga caaatgctag aatatatcct ggtaggttga tgaactggtt gataatgggc      720
caaaattacc acttagttca ccattttatgg ccatcaatac catggtttga atacaaacct      780
gcatatgaag ccacaaagcc attgttagat tctaaaggta gtccacaaag attaggtata      840
```

```
ttcgagacaa ggagagatgg ctataacttc ttatacgata tattagttgg tgttagatca        900
cacaagagaa gaagggtaa aatgagaagg gccgcaaggt tcatgccaat gagatccttc         960
caaagacact ggttaggttt cgtcgataga atcgccatca aaaccgaacc tagaagacct       1020
ttaaagagat                                                              1030

<210> SEQ ID NO 6
<211> LENGTH: 996
<212> TYPE: DNA
<213> ORGANISM: Synechococcus elongatus

<400> SEQUENCE: 6
atgtcagagg ctcaaacgcc cctgacagta ccgaagaagt tcttggtgc tccaggaggc          60 ttcaaccca ccgtcgcact cttcttggca ggttatacct gcgcggcgct ctcagttttg         120
gggtactggt gctggagttg gccccactgg ctatctttcc ttctgagtgt cacagcctta        180
catttggtag gcaccgtcat tcacgatgcc tctcataatg tggctcacgc cagtcgcatt        240
ctgaatgcga ttttgggaca tggcagtgca ctattgctgg gctttacttt tccggtgttt        300
acgcgggttc acctgcaaca tcacgcccac gtcaacgatc caagaacga tcccgaccac         360 atcgttttcca ccttttgggcc gctgtggttg atcgcaccgc gcttcttcta tcacgagatc      420
tatttcttcc agcgccgcct ttggaagaaa tttgaattac tcgaatggtt cctcagtcgc        480
gctgtggtca tcggcatctt tgcctgcggc gtcaagtttg gcttcctggg cttcctgatg        540
aactactggc tggctccagc cttggtcgtt ggcattgccc taggactctt cttcgactat        600
ttaccccacc gccccttcca agagcgcaac cgctggcgca atgcacgggt ctatcccggt        660
caggtgatga acatcctgat catgggtcag aactatcacc tgatccatca cctctggcca       720
tcgatcccct ggtatctcta ccgaccggcc taccacgcta ccaagccgtt gttggaccta       780
cgccagtcgc cgcaaacgct cgggattctc tccagcaaaa aagatttctg aactttatc        840 tacgacgttt tcatcggcat ccgcattcac caatcgcacg aggctgagcc gcagagctcc        900
gtcgttcctg aaacgaagtc gagtgaatca gccgttctcg caaaagctcc gatgtctgcc        960
acagaagact ctcgtgagcc agccttgacg aagtag                                 996

<210> SEQ ID NO 7
<211> LENGTH: 1035
<212> TYPE: DNA
<213> ORGANISM: Prochlorococcus marinus

<400> SEQUENCE: 7
atgacaaata ccttaaatac aactattcat aatgatttac ccccaaaatt ccaatcgtca         60
agtttttggc aaaagcgcat taagattat ctagatccac taatttttt caatcccact          120 ttaggcttat ttattggtgg ttatgcaata gcatttctct ctatatggca atggtataaa        180
ggggtatggc cacttcctgt actagttggg cttgcattcc ttctctctca tatggaaggg        240
actgttatcc atgatgcctg tcacaaagca gctcatccta taaatggat aaatcaggct         300 atgggtcatg gcgcagcaat attattaggt tttagttttc cagttttcac tagagtccat       360
cttcaacatc actctcatgt caatgatccc aagaatgacc ctgatcatat agtcagtact       420
tttggcccag tctggttaat tgctccaagg ttttttatc atgaatattt cttttttcaa       480
aggaaactct ggaggaaata tgaactaatg caatggggcc tagagcgatc cattttcata       540
acaattgttt tagctggtgt tcattttaat ttcatgaacg taatttataa ccttggtttt       600
ggtccagcac taatggttgg agttactctt ggaatattct ttgactacct ccctcatcgc       660
```

```
ccatttatgg ctcgcaataa atggaagaat tcaagggtat atccaagtcg agtaatgaat    720
atactgataa tgggccaaaa ttatcatcta gttcatcatt tatggccttc aattccttgg    780
tttgaatata agccagctta tgaagcaact aaaccacttt tagatcagaa agggtcacca    840
caaagaatgg gtattttga atcaaaaaaa gatagttta atttccttta tgacattatt    900
ttaggaataa gaagtcacaa aaaagtagg agtaaaatga ggcctctagc gaacttaatc    960
ccaacgaaaa aattgagaag aaaatggctt tatattcttc ataaaactgc aatcatccca   1020
gataaaattg attaa                                                    1035

<210> SEQ ID NO 8
<211> LENGTH: 1612
<212> TYPE: DNA
<213> ORGANISM: Zea mays

<400> SEQUENCE: 8
atgggtttga gtggtgccac tatctcagca ccattaggct gctgtgtttt aagatgcggc     60
gctgtgggtg gtggaaaagc attgaaagct gatgctgaaa ggtggagaag agctggttgg    120
tccagaaggg taggtggtcc aaaagtgaga tgcgtggcaa ccagagaaaca tgatgaaact    180 gcagcagtgg gtgcagctgt tggcgtcgat tttgctgatg aggaagacta tagaaaagga    240
ggtggaggag aattgttgta tgttcagatg caaagtacaa agcctatgga gagtcaatct    300
aagatagctt ctaagttgtc tccaatcagt gatgaaaaca ctgtcttgga cttagttatt    360
ataggatgtg gcccagcagg tttatcattg gcttctgaat cagcaaagaa aggttttgact   420 gttggcttaa tcggtcctga cttgcctttt acaaataact atggtgtttg ggaggatgaa    480
ttcaaagatt tgggtttgga atcctgtatt gaacacgtat ggaaagatac tatagtttat    540
ttggataata ataagcctat tttgattgga agatcttatg gcagagtaca cagagattta    600
ttacacgagg aattattaaa gagatgttac gaagccggtg tcacatactt aaactctaaa    660
gtggataaga taattgaaag tccagacggc catagagtag tttgttgtga taaaggtagg    720
gaaatcatat gtaggttggc aatcgtcgct tcaggagccg ccagtggtag gttattggaa    780
tacgaggtcg gcggccccag agtttgtgtc cagacagctt atggagtaga ggtagaagtc    840
gagaacaatc cctatgaccc atccttaatg gtctttatgg attacagaga ttgcttcaaa    900
gaagaatttt ctcatacaga acaagaaaac cccactttct gtatgcaat gcctatgtca    960 ccaaccagag tgttctttga agagacctgc ttagcatcta agatgcaat gtcatttgat   1020 ttattaaaga aaagattgat gtacagattg aatgctatgg aataaggat attgaaggtg   1080 tatgaagaag aatggagtta catcccagtt ggtggttcat tgcctaacac agaccaaaag   1140
aatttagctt ttggtgctgc tgcaagtatg gttcatcctg ccaccggata ttccgttgtt   1200
aggtccttgt ccgaagcacc taggtacgct tcagtaattt cagacatttt aggtaataga   1260
gttcccgctg aatacatgtt gggaaactcc caaaattact caccatcaat gttagcctgg   1320
aggaccttgt ggccacaaga gagaaagagg cagaggtctt tcttcttatt cggattagcc   1380
ttgattattc aattaaacaa tgagggtatt caaactttct tcgaggcctt ctttagagta   1440
ccaagatgga tgtggagagg tttcttaggt tctacattgt cttctgttga cttgatctta   1500
ttttctttct atatgttcgc cattgcccca aatcagttga gaatgaattt agttagacat   1560
ttgttatctg accctacagg ttcctctatg attaagactt atttaacttt at           1612

<210> SEQ ID NO 9
```

<211> LENGTH: 1964
<212> TYPE: DNA
<213> ORGANISM: Arabidopsis thaliana

<400> SEQUENCE: 9

| | | | | | |
|---|---|---|---|---|---|
| ctctctttct | gggaagaaga | taattgtctc | catctccatg | aagctactgc | ttctgggtaa | 60 |
| gttttgtggt | cttcgttcat | cttttctcta | gcaatttagt | attccatttt | ctcaatccct | 120 |
| ctggttagaa | atcgtgtccg | gtgattttttg | aattatatcc | ttttggtgtt | ttcttcgatt | 180 |
| ttgggggaat | tcgatggata | tctctgttgaa | aacacccaac | aagctcgatt | ttttcatccc | 240 |
| tcagtttcat | gggtttgaga | gattatgcag | taacaatcca | taccattcaa | gggttaggct | 300 |
| tggtgtgaag | aaaagggcta | tcaaaattgt | ctctagtgta | gtgagtggta | gcgctgctct | 360 |
| tttggatctt | gttcctgaaa | ctaagaagga | gaatcttgac | tttgagcttc | ctttgtacga | 420 |
| cacttccaag | agtcaagttg | ttgatttggc | tattgttggt | ggtggtcctg | ctggtttagc | 480 |
| cgtggctcag | caggtttctg | aagctggact | ctctgtttgt | tccattgatc | cttctcctaa | 540 |
| gctcatatgg | cctaacaatt | atggagtttg | ggttgatgag | tttgaggcta | tggatttact | 600 |
| agactgcctg | gataccacat | ggtctggtgc | tgttgtctat | gtcgatgaag | gtgtcaagaa | 660 |
| ggatttgagc | cggccttatg | ggagagttaa | ccggaaacag | ctcaaatcca | aaatgcttca | 720 |
| gaaatgtatt | accaacggtg | ttaaatttca | tcagtctaag | gtcactaatg | tggttcacga | 780 |
| ggaggcaaac | tccactgtgg | tctgcagtga | cggtgtaaag | attcaggctt | ccgtggttct | 840 |
| tgatgccact | gggttttccc | gatgcttggt | tcagtatgac | aaaccttaca | accctgggta | 900 |
| ccaagtagct | tacgggattg | tagctgaagt | tgatggtcac | ccattcgatg | tagacaaaat | 960 |
| ggtgttcatg | gattggagag | acaaacatct | ggactcatat | cctgagctga | agaacggaa | 1020 |
| cagcaagatc | ccaacgttct | tgtacgctat | gccatttttct | tccaaccgaa | tatttcttga | 1080 |
| agaaacttct | ttagttgcta | gacctggtct | gagaatggaa | gatatccaag | aaagaatggc | 1140 |
| tgctagactg | aaacatctgg | ggatcaatgt | gaagaggatt | gaggaagacg | agcgttgtgt | 1200 |
| gatcccgatg | ggcggtcctt | taccagtctt | acctcaacgg | gttgtgggga | ttggtgggac | 1260 |
| agcaggaatg | gttcatcctt | caactggtta | catggttgct | aggactcttg | cagctgcacc | 1320 |
| aatagttgca | aatgccattg | tgagataccct | cggttcacca | agtagtaata | gcctgagagg | 1380 |
| agatcaactc | tctgctgagg | tttggagaga | cttgtggcct | atcgaacggc | gtagacagag | 1440 |
| ggagttcttc | tgttttggaa | tggatattct | gctgaaactc | gatttagacg | ctactagaag | 1500 |
| gttctttgat | gcattctttg | atctgcaacc | tcattactgg | cacgattct | tgtcttccag | 1560 |
| gctgtttctc | ccggaactgt | tggtcttcgg | gttgtcgctc | ttctcacacg | cttccaatac | 1620 |
| ctcaagattg | gagatcatga | caaagggggac | tgttcctctt | gctaagatga | tcaacaatttt | 1680 |
| ggtacaagat | agagactaag | gaccagaaac | ttagacatat | aagtacatct | gttctttggt | 1740 |
| tcttgaccag | tagtatatcc | gcattgcaag | tcgttggata | attgtgtata | aaccacagat | 1800 |
| cataacctga | atccttgtga | aatcaaattg | ttactactag | ttcattaaaa | ttaatacttt | 1860 |
| gtgctgcatt | gtgtttcacc | aactcttgta | aatccaaaac | tagaggcaaa | atgtaataag | 1920 |
| ataaagagt | ggattttgaa | cacaaaagca | aatctttcaa | actc | | 1964 |

<210> SEQ ID NO 10
<211> LENGTH: 1158
<212> TYPE: DNA
<213> ORGANISM: Xanthobacter autotrophicus

<400> SEQUENCE: 10

-continued

```
atggacatcg tcttcgtcgg cgccggactt gccaattgcc ttatggcggc gcgcctcgcg    60
gcccagcgtc ccggccttca catgctgctg ctggaagccg gcgagagcgt gggcggcaat   120
cacagctggt cctgccacga cagcgatctc actgccgcgc agcgcgcctt cctcgctccc   180
ttccagagct atctctgggc cgggcacggg gtgcattttc ccgcttttc gcgcacgctc    240 aaaggcggct acgccaccat ttcctccgag cgcatggccg aggtgatgaa tgagcgcctg   300
tgcgccgcca tccgcaccaa tgcccgcgtc gcccatgtgg cgcccgacca cgtggtgctg   360
gagggcggcg agcgcatcga cgcccgcgcc gtggtggacg ggcgcggccc actcgcctcg   420
cgccatctcg acctcggcta ccagaccttc ctggggcagg aactgcgtat gtctcggccc   480
catggcctca cccgccccat catcatggat gcgcgggtgg agcagctggg cggttaccgc   540
ttcgtctatg tgctgccgct ggacgatgac acgctgctgg tggaagacac ctattatgcc   600
gacggcccgg atcttcccgc cgatgccttg cgcggccgca tttccgccta tgccgcggcg   660
cagggctggg ccgtggatta tgtggtgcgg gaggaggacg gcatcttgcc gatagcgttg   720
ggcggcgaca tcaacgcctt tcttgccgag acgccttcgg gcgtcgcgcc cgccggactg   780
cgggcaggcc tgttccaccc caccaccggc tacagcctgc ccgacgccat ggccctggcc   840
gactcggtga gcgcgcttgc cgaccttttcc ggccccgcgc tttcggcggc agtgcgcagc   900
catgcggcgg cggcgtggaa cgggcgcggc ttcttccgcc tgctcaaccg catgctgttc   960
cgcgctgccg atccggagcg cgcgctatgcc attctccagc gcttctacgg gctgtcggaa  1020
gacctgatcg cccgtttcta cgccgatcgc ctcacccttg ccgacaaggc gcgcatcctt  1080
tcgggccgcc caccgtatc ggtgttcagg gcgctctcct gccttgttga gacgaaagcc  1140
gcacccggtt ccccatga                                                1158
```

<210> SEQ ID NO 11
<211> LENGTH: 29
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(15)
<223> OTHER INFORMATION: n is a, c, g, or t
<220> FEATURE:
<221> NAME/KEY: misc_feature
<222> LOCATION: (18)..(20)
<223> OTHER INFORMATION: n is a, c, g, or t

<400> SEQUENCE: 11
tctagagaaa gannngannn tactagatg                                      29

<210> SEQ ID NO 12
<211> LENGTH: 13
<212> TYPE: DNA
<213> ORGANISM: Artificial Sequence
<220> FEATURE:
<223> OTHER INFORMATION: Synthetic Construct

<400> SEQUENCE: 12
tcacacagga aag                                                       13

<210> SEQ ID NO 13
<211> LENGTH: 129
<212> TYPE: DNA
<213> ORGANISM: Artificial Sequence
<220> FEATURE:

```
<223> OTHER INFORMATION: Synthetic Construct

<400> SEQUENCE: 13
ccaggcatca aataaaacga aaggctcagt cgaaagactg ggcctttcgt tttatctgtt      60
gtttgtcggt gaacgctctc tactagagtc acactggctc accttcgggt gggcctttct     120
gcgtttata                                                             129
```